(12) United States Patent
Kawata et al.

(10) Patent No.: US 11,313,858 B2
(45) Date of Patent: Apr. 26, 2022

(54) SAMPLE ANALYSIS DEVICE, SAMPLE ANALYSIS SYSTEM, AND METHOD OF MEASURING LUMINESCENCE OF A SAMPLE

(71) Applicant: PHC HOLDINGS CORPORATION, Tokyo (JP)

(72) Inventors: Hiroto Kawata, Ehime (JP); Kazuya Kondoh, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 458 days.

(21) Appl. No.: 16/143,253

(22) Filed: Sep. 26, 2018

(65) Prior Publication Data

US 2020/0096504 A1   Mar. 26, 2020

(51) Int. Cl.
| | | |
|---|---|---|
| *G01N 21/75* | (2006.01) | |
| *G01N 35/00* | (2006.01) | |
| *B01L 3/00* | (2006.01) | |
| *G01N 33/543* | (2006.01) | |
| *G01N 21/64* | (2006.01) | |

(Continued)

(52) U.S. Cl.
CPC ........ *G01N 33/54373* (2013.01); *B01L 3/502* (2013.01); *B01L 3/5027* (2013.01); *G01N 21/6428* (2013.01); *G01N 21/66* (2013.01); *G01N 21/75* (2013.01); *G01N 21/76* (2013.01); *G01N 33/54326* (2013.01); *B01L 2200/12* (2013.01); *B01L 2400/0409* (2013.01); *G01N 2021/6439* (2013.01)

(58) Field of Classification Search
None
See application file for complete search history.

(56) References Cited

U.S. PATENT DOCUMENTS 5,798,263 A * 8/1998 Wood .................. G01N 21/763
                                                        250/361 C
6,469,311 B1 * 10/2002 Modlin ............. G01N 21/6408
                                                        250/559.4

(Continued)

FOREIGN PATENT DOCUMENTS

| JP | H07-500910 A | 1/1995 |
|---|---|---|
| JP | 2007-003362 A | 1/2007 |

(Continued)

OTHER PUBLICATIONS

Extended European Search Report issued in corresponding European Patent Application No. 18196735.7, dated Feb. 6, 2019.

*Primary Examiner* — Neil N Turk
(74) *Attorney, Agent, or Firm* — McDermott Will & Emery LLP

(57) ABSTRACT

A sample analysis device includes: a motor to rotate a sample analysis substrate with a sample introduced thereon around a rotation axis of the sample analysis substrate; a drive circuit to drive the motor; a photodetector to measure a number of photons associated with a luminescence from the sample being transmitted through a window of a measurement chamber of the sample analysis substrate; and a control circuit to calculate a measurement value of the luminescence of the sample by using a number of photons measured by the photodetector while the motor rotates the sample analysis substrate.

11 Claims, 13 Drawing Sheets

(51) Int. Cl.
*G01N 21/76* (2006.01)
*G01N 21/66* (2006.01)

(56) References Cited

U.S. PATENT DOCUMENTS

| | | | |
|---|---|---|---|
| 2002/0060298 A1* | 5/2002 | Endo | G02B 21/0032 |
| | | | 250/492.22 |
| 2002/0182108 A1* | 12/2002 | Ishihara | G01N 35/021 |
| | | | 422/62 |
| 2009/0189089 A1 | 7/2009 | Bedingham et al. | |
| 2010/0062415 A1* | 3/2010 | Schwoebel | G01N 33/582 |
| | | | 435/5 |
| 2011/0104009 A1 | 5/2011 | Kawamura et al. | |
| 2017/0141708 A1* | 5/2017 | Kondoh | H02P 6/16 |
| 2018/0003642 A1* | 1/2018 | Tomoda | G01N 33/54326 |

FOREIGN PATENT DOCUMENTS

| | | |
|---|---|---|
| JP | 2007-147472 A | 6/2007 |
| JP | 2011-196849 A | 10/2011 |
| JP | 2015-081884 A | 4/2015 |
| WO | 93/08893 A1 | 5/1993 |

\* cited by examiner

SAMPLE ANALYSIS DEVICE, SAMPLE ANALYSIS SYSTEM, AND METHOD OF MEASURING LUMINESCENCE OF A SAMPLE

BACKGROUND

The present application relates to a sample analysis device, a sample analysis system, and a method of measuring luminescence of a sample.

Techniques have been known which utilize a substrate for sample analysis (hereinafter "sample analysis substrate") in order to analyze a specific component within an analyte, such as urine or blood. For example, Japanese Patent Publication No. 7-500910 discloses a technique that utilizes a disk-shaped sample analysis substrate, on which channels, chambers, and the like are formed. In this technique, the sample analysis substrate is allowed to rotate, etc., thereby effecting transfer, distribution, mixing of solutions, analysis of components within an analyte solution, and so on. The specific component is quantified by detecting light which is generated through immunoreaction, for example.

SUMMARY

When the concentration of the specific component in the analyte is low, the luminescence due to immunoreaction is also weak. In order to detect a specific component of low concentration with high sensitivity, it is necessary to accurately measure the intensity of subtle luminescence.

A non-limiting, illustrative embodiment of the present application provides a sample analysis device, a sample analysis system, and a method of measuring luminescence of a sample which allows subtle luminescence to be measured with high sensitivity.

A sample analysis device according to the present disclosure is a sample analysis device which, by rotating a sample analysis substrate including a measurement chamber and a shading portion, the measurement chamber having a window, allows a sample that is introduced onto the sample analysis substrate to be transferred to the measurement chamber, allows the sample to undergo luminescence in the measurement chamber, and measures the luminescence. The sample analysis device comprises: a motor to rotate the sample analysis substrate with the sample introduced thereon around a rotation axis of the sample analysis substrate; a drive circuit to drive the motor; a photodetector to measure a number of photons associated with the luminescence from the sample being transmitted through the window of the measurement chamber; and a control circuit to calculate a measurement value of the luminescence of the sample by using a number of photons measured, by the photodetector, while the motor rotates the sample analysis substrate.

According to the present disclosure, there is provided a sample analysis device, a sample analysis system, and a method of measuring luminescence of a sample which allows subtle luminescence to be measured with high sensitivity.

DETAILED DESCRIPTION

Assay techniques for components within a sample such as urine or blood may utilize a combination reaction between the analyte being the subject for analysis and a ligand which specifically binds to the analyte. Examples of such assay techniques include immunoassay techniques and genetic diagnosis techniques. A sample such as urine or blood may be referred to as an analyte in the fields of medicine and pharmacy.

Examples of immunoassay techniques are competitive assays and non-competitive assays (sandwich immunoassay). Examples of genetic diagnosis techniques are genetic detection techniques based on hybridization. In these immunoassay techniques and genetic detection techniques, magnetic particles (which may also be referred to as "magnetic beads", "magnetism particles", "magnetism beads", etc.) are used, for example. As an example of such assay techniques, a sandwich immunoassay utilizing magnetic particles will be specifically described.

Figure 1:
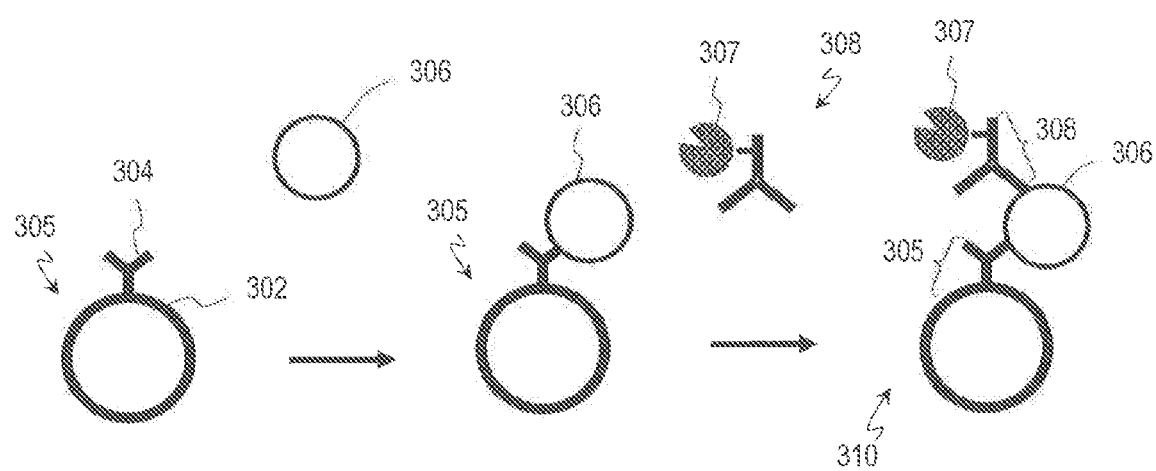
FIG. 1 is an exemplary schematic diagram describing a sandwich immunoassay utilizing magnetic particles.

As shown in FIG. 1, first, a primary antibody 304 having a magnetic particle 302 immobilized to whose surface (hereinafter referred to as the "magnetic-particle-immobilized antibody 305") and an antigen 306 that is contained in a sample for measurement are allowed to bind through an antigen-antibody reaction. Next, a secondary antibody to which a label substance 307 has bound (hereinafter referred to as a "labeled antibody 308") and the antigen 306 are allowed to bind through an antigen-antibody reaction. As a result, a composite 310 is obtained in which the magnetic-particle-immobilized antibody 305 and the labeled antibody 308 have bound to the antigen 306.

A signal which is based on the label substance 307 of the labeled antibody 308 that has bound to the composite 310 is detected, and an antigen concentration is measured in accordance with the amount of detected signal. Examples of the label substance 307 include enzymes (e.g., peroxidase, alkaline phosphatase, and luciferase), chemiluminescent substances, electrochemiluminescent substances, and fluorescent substances. In accordance with each such label substance 307, dye, luminescence, fluorescence, or other signals are detected. Although the light to be detected is not emitted from the sample itself, component analysis of the sample consists in measuring the concentration of the antigen 306 or the like within the sample, and it is the composite 310 with the antigen 306 having bound thereto that undergoes luminescence; therefore, for ease of understanding, the sample will be said to be undergoing luminescence in the present specification.

As a photodetector for detecting subtle light, the inventors have considered the use of a photon counter which counts the number of photons that are associated with luminescence. Since a photon counter has high detection sensitivity, it may also detect stray light that unavoidably occurs from anything but the target of measurement. Moreover, principlewise, a photon counter is susceptible to temperature influences during measurements. The inventors have taken these problems into account, and arrived at a novel sample analysis device. A sample analysis device, a sample analysis system, and a method of measuring luminescence of a sample according to the present disclosure may be summarized as follows.

(Item 1) A sample analysis device which, by rotating a sample analysis substrate including a measurement chamber and a shading portion, the measurement chamber having a window, allows a sample that is introduced onto the sample analysis substrate to be transferred to the measurement chamber, allows the sample to undergo luminescence in the measurement chamber, and measures the luminescence;

the sample analysis device comprising:

a motor to rotate the sample analysis substrate with the sample introduced thereon around a rotation axis of the sample analysis substrate;

a drive circuit to drive the motor;

a photodetector to measure a number of photons associated with the luminescence from the sample being transmitted through the window of the measurement chamber; and a control circuit to calculate a measurement value of the luminescence of the sample by using a number of photons, the number of photons being measured by the photodetector while the motor rotates the sample analysis substrate.

(Item 2) The sample analysis device of item 1, wherein, the photodetector outputs at least one first measurement value and at least one second measurement value while the sample analysis substrate rotates; and the control circuit calculates a measurement value of the luminescence of the sample by correcting the at least one first measurement value with the at least one second measurement value.

(Item 3) The sample analysis device of item 2, wherein, the photodetector outputs a plurality of measurement values obtained through one complete turn of the sample analysis substrate; and the control circuit compares each of the plurality of measurement values against a first threshold and against a second threshold, and determines any one of the plurality of measurement values that is equal to or greater than the first threshold to be the at least one first measurement value and any one of the plurality of measurement values that is equal to or less than the second threshold to be the at least one second measurement value.

(Item 4) The sample analysis device of item 2, further comprising a rotation angle detection circuit to detect a rotation angle of the sample analysis substrate and generate a rotation angle signal, wherein, the photodetector outputs a plurality of measurement values obtained while the sample analysis substrate makes one complete turn; and the control circuit performs the above calculation by using a measurement value which is measured by the photodetector when the rotation angle is in a first angle range and a measurement value which is measured by the photodetector when the rotation angle is in a second angle range, respectively as the at least one first measurement value and as the at least one second measurement value.

(Item 5) The sample analysis device of item 4, wherein the second angle range is greater than the first angle range.

(Item 6) The sample analysis device of item 4, wherein the control circuit compares against a third threshold a measurement value which is measured by the photodetector when the rotation angle is not in the first angle range, and generates a signal indicating a measurement error when the measurement value is equal to or greater than the third threshold.

(Item 7) The sample analysis device of item 1, wherein, the sample analysis substrate includes another measurement chamber in which another sample to undergo luminescence is retained;

the photodetector further outputs at least one third measurement value while the sample analysis substrate makes one complete turn; and the control circuit calculates a measurement value of the luminescence of the other sample by correcting the at least one third measurement value with the at least one second measurement value.

(Item 8) The sample analysis device of item 1, wherein the photodetector includes: a photomultiplier element to receive a photon or photons and generate a pulse signal or pulse signals in accordance with the number of photons; and a photon counter to count the pulse signal.

(Item 9) The sample analysis device of item 1, further comprising:

a rotation angle detection circuit to detect a rotation angle of the sample analysis substrate and generate a rotation angle signal; and a reference clock generation circuit to generate a reference clock signal, wherein, the photodetector includes a photomultiplier element to generate a photon pulse signal in accordance with the number of photons; and by using the reference clock signal, the rotation angle signal, and the photon pulse signal, the control circuit calculates a photon count distribution signal across rotation angles that has been corrected so that an equal counting time exists for the number of photons per unit rotation angle.

(Item 10) The sample analysis device of item 9, wherein, the control circuit counts the photon pulse signal on the basis of the rotation angle signal and calculates a photon count distribution across rotation angles, counts the reference clock signal on the basis of the rotation angle signal and calculates a clock count distribution across rotation angles, and corrects the photon count distribution with the clock count distribution to calculate the corrected photon count distribution signal.

(Item 11) The sample analysis device of item 9, wherein, the control circuit counts the photon pulse signal on the basis of the reference clock signal and calculates a photon count distribution on the time axis, counts the rotation angle signal on the basis of the reference clock signal and calculates a rotation angle distribution on the time axis, and corrects the photon count distribution with the rotation angle distribution to calculate the corrected photon count distribution signal.

(Item 12) The sample analysis device of item 9, wherein, the control circuit calculates a measurement value of the luminescence of the sample by correcting a first measurement value which exists in the corrected photon count distribution signal when the rotation angle is in a first angle range with a second measurement value which exists in the corrected photon count distribution signal when the rotation angle is in a second angle range.

(Item 13) A sample analysis system comprising:

a sample analysis substrate including a measurement chamber and a shading portion, the measurement chamber having a window; and the sample analysis device of item 1.

(Item 14) A sample analysis system comprising:

a sample analysis substrate including a measurement chamber and a shading portion, the measurement chamber having a window; and the sample analysis device of item 9.

(Item 15) A method of measuring luminescence of a sample, the method comprising the steps of:

introducing a sample onto a sample analysis substrate including a measurement chamber and a shading portion, the measurement chamber having a window; and measuring a number of photons associated with luminescence from the sample with a photodetector which measures a number of photons, while rotating the sample analysis substrate with the sample introduced thereon.

(Item 16) The measurement method for measuring luminescence of a sample of item 15, wherein, in the measuring step, the photodetector outputs at least one first measurement value and at least one second measurement value while the sample analysis substrate rotates; and the method further comprises a step of correcting the at least one first measurement value with the at least one second measurement value.

(Item 17) The measurement method for measuring luminescence of a sample of item 16, wherein, in the measuring step, the photodetector outputs a plurality of measurement values obtained through one complete turn of the sample analysis substrate; and the correcting step compares each of the plurality of measurement values against a first threshold and against a second threshold, and determines any one of the plurality of measurement values that is equal to or greater than the first threshold to be the at least one first measurement value and any one of the plurality of measurement values that is equal to or less than the second threshold to be the at least one second measurement value.

(Item 18) The measurement method for measuring luminescence of a sample of item 16, wherein, in the measuring step:

a rotation angle of the sample analysis substrate is detected, and a rotation angle signal is generated;

the photodetector outputs a plurality of measurement values obtained through one complete turn of the sample analysis substrate; and the correcting step performs the above calculation by using a measurement value which is measured by the photodetector when the rotation angle is in a first angle range and a measurement value which is measured by the photodetector when the rotation angle is in a second angle range, respectively as the at least one first measurement value and as the at least one second measurement value.

(Item 19) The measurement method for measuring luminescence of a sample of item 18, wherein the second angle range is greater than the first angle range.

(Item 20) The measurement method for measuring luminescence of a sample of item 18, wherein the measurement step compares against a third threshold a measurement value which is measured by the photodetector when the rotation angle is not in the first angle range, and generates a signal indicating a measurement error when the measurement value is equal to or greater than the third threshold.

(Item 21) The measurement method for measuring luminescence of a sample of item 15, wherein, the sample analysis substrate includes another measurement chamber in which another sample to undergo luminescence is retained;

the measurement step further outputs at least one third measurement value while the sample analysis substrate makes one complete turn; and the correcting step calculates a measurement value of the luminescence of the other sample by correcting the at least one third measurement value with the at least one second measurement value.

(Item 22) The measurement method for measuring luminescence of a sample of item 15, wherein, the measuring step comprises:

a step of generating a reference clock signal, and, while detecting a rotation angle of the sample analysis substrate and generating a rotation angle signal, detecting a photon or photons associated with luminescence from the sample and generating a photon pulse signal in accordance with the number of photons; and a step of calculating a photon count distribution signal across rotation angles that has been corrected so that an equal counting time exists for the number of photons per unit rotation angle, by using the reference clock signal, the rotation angle signal, and the photon pulse signal.

(Item 23) The measurement method for measuring luminescence of a sample of item 22, wherein, the calculating step counts the photon pulse signal on the basis of the rotation angle signal and calculates a photon count distribution across rotation angles, counts the reference clock signal on the basis of the rotation angle signal and calculates a clock count distribution across rotation angles, and corrects the photon count distribution with the clock count distribution to calculate the corrected photon count distribution signal.

(Item 24) The measurement method for measuring luminescence of a sample of item 22, wherein, the calculating step counts the photon pulse signal on the basis of the reference clock signal and calculates a photon count distribution on the time axis, counts the rotation angle signal on the basis of the reference clock signal and calculates a rotation angle distribution on the time axis, and corrects the photon count distribution with the rotation angle distribution to calculate the corrected photon count distribution signal.

(Item 25) The measurement method for measuring luminescence of a sample of item 22, further comprising a step of, after the calculating step, calculating a measurement value of the luminescence of the sample by correcting a first measurement value which exists in the corrected photon count distribution signal when the rotation angle is in a first angle range with a second measurement value which exists in the corrected photon count distribution signal when the rotation angle is in a second angle range.

Hereinafter, with reference to the drawings, a sample analysis device, a sample analysis system, and a method of measuring luminescence of a sample according to the present disclosure will be described. The sample analysis system according to the present disclosure includes a sample analysis device and a sample analysis substrate. The sample analysis system according to the present disclosure is applicable to a method of analysis utilizing the aforementioned magnetic particles. Hereinafter, the respective component elements will be described.

First Embodiment (Sample Analysis Substrate 100)

Figure 2A:
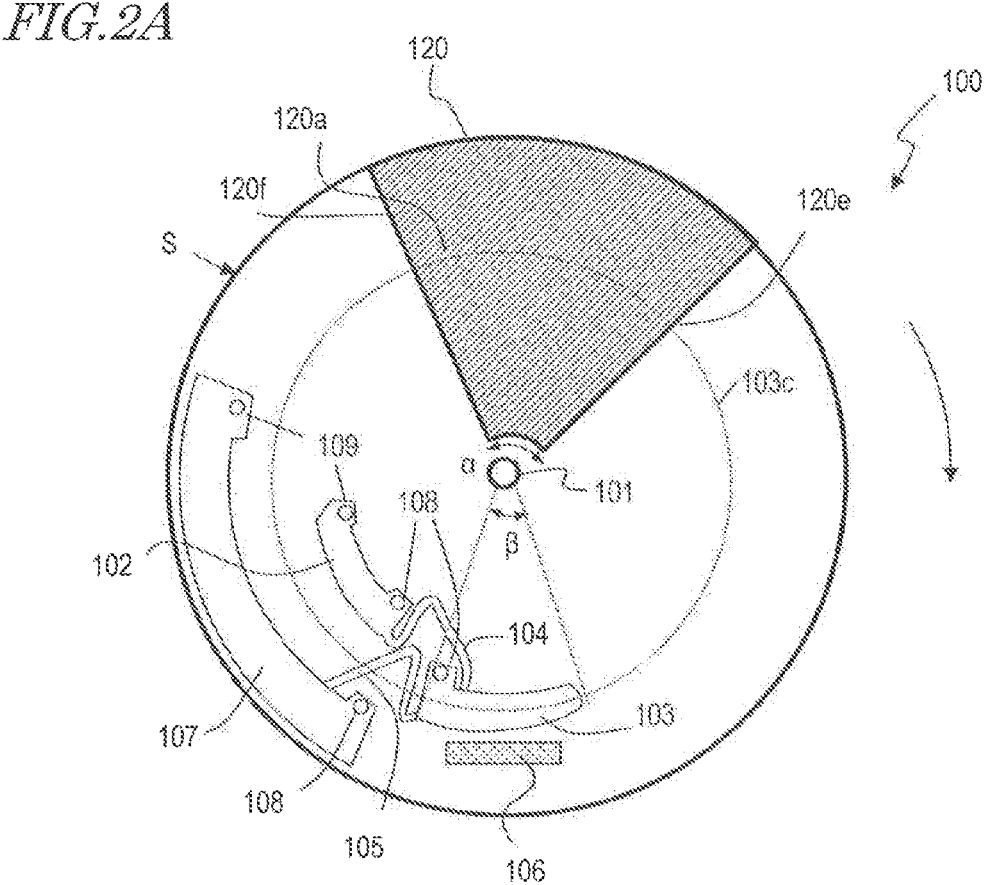
FIG. 2A is a plan view showing an exemplary structure of a sample analysis substrate.
Figure 2B:
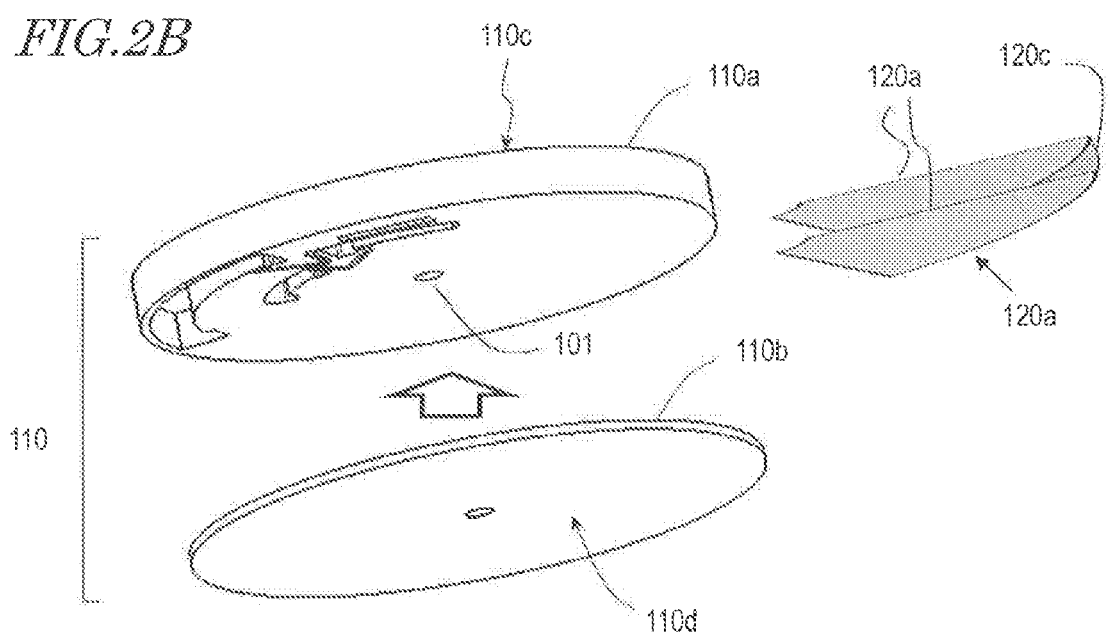
FIG. 2B is an exploded perspective view of a sample analysis substrate.

FIG. 2A and FIG. 2B are a plan view and an exploded perspective view, respectively, of the sample analysis substrate 100. The sample analysis substrate 100 includes a substrate 110 having a rotation axis 101 and a plate shape with a predetermined thickness along a direction which is parallel to the rotation axis 101, and a light-shield cap 120. Although the substrate 110 of the sample analysis substrate 100 has a circular shape in the present embodiment, it may alternatively be shaped as a polygon, an ellipse, a sector, or the like. The substrate 110 has two principal faces 110c and 110d. In the present embodiment, the principal face 110c and the principal face 110d are parallel to each other, and the thickness of the substrate 110 as defined by an interspace between the principal face 110c and the principal face 110d is constant irrespective of position within the substrate 110. However, the principal faces 110c and 110d do not need to be parallel. For example, the two principal faces may be partly non-parallel or parallel, or be entirely non-parallel. Moreover, at least one of the principal faces 110c and 110d of the substrate 110 may have a structure with recesses or protrusions. The sample analysis substrate 100 includes a reaction chamber 102 located in the substrate 110, a measurement chamber 103, a recovery chamber 107, a channel 104, and a channel 105.

In the present embodiment, the substrate 110 of the sample analysis substrate 100 is composed of a base substrate 110a and a cover substrate 110b. The respective spaces of the reaction chamber 102, the measurement chamber 103, and the recovery chamber 107 are formed within the base substrate 110a, and as the cover substrate 110b covers over the base substrate 110a, a top and a bottom of each space are created. In other words, the respective spaces of the reaction chamber 102, the measurement chamber 103, and the recovery chamber 107 are defined by at least one inner face of the sample analysis substrate 100. The channel 104 and the channel 105 are also formed in the base substrate 110a, and as the cover substrate 110b covers over the base substrate 110a, a top and a bottom of each space of the channel 104 and the channel 105 are created. Thus, the reaction chamber 102, the measurement chamber 103, the recovery chamber 107, and the channel 104 and channel 105 are enclosed within the substrate 110.

In at least one of the principal face 110c and the principal face 110d, the measurement chamber 103 has a window through which the luminescence occurring from a composite 310 containing a sample to be retained in the measurement chamber 103 is transmitted. In the present embodiment, the base substrate 110a and the cover substrate 110b are utilized respectively as an upper face and a lower face. The substrate 110 may be formed of a transparent resin which may be acrylic, polycarbonate, polystyrene, or the like. As used herein, "transparent" refers to the ability to transmit light of a wavelength region that is detectable by a photodetector 209 described below, within the luminescence occurring from the composite 310.

The light-shield cap 120, which includes a pair of shading portions 120a and a connecting portion 120c, is attached to the substrate 110 so that the shading portions 120a partially cover the principal faces 110c and 110d of the substrate 110. In the present embodiment, each shading portion 120a has a substantial sector shape. The shading portions 120a are made of a material that does not transmit luminescence occurring from the composite 310. Preferably, each shading portion 120a is provided at a position on the principal face 110c or 110d of the substrate 110 that is opposed to the light-receiving surface of the photodetector 209. Moreover, as shown in FIG. 2A, a central angle $\alpha$ of the region of the principal face 110c or the principal face 110d where the shading portion 120a is located is preferably larger than a central angle $\beta$ of the region where the measurement chamber 103 is located.

As has been described with reference to FIG. 1, the reaction chamber 102 is a reaction field in which the magnetic-particle-immobilized antibody 305, an analyte containing the antigen 306, and the labeled antibody 308 are allowed to react and form the composite 310. There is no particular limitation as to the shape of the reaction chamber 102. In the present embodiment, the sample analysis substrate 100 includes the reaction chamber 102 as a reaction field where the composite 310 is allowed to form. Various means may be adopted in transferring the magnetic-particle-immobilized antibody 305, a sample containing the antigen 306, and the labeled antibody 308 to the reaction chamber 102. For example, a mixed solution in which the magnetic-particle-immobilized antibody 305, the sample containing the antigen 306, and the labeled antibody 308 have been previously mixed may be weighed out, and the mixed solution may be injected into the reaction chamber 102 in the sample analysis substrate 100. Moreover, the sample analysis substrate 100 may include chambers respectively retaining the magnetic-particle-immobilized antibody 305, the sample containing the antigen 306, and the labeled antibody 308, and a channel (e.g., a capillary channel) via which each chamber and the reaction chamber 102 are coupled. In this case, the magnetic-particle-immobilized antibody 305, the sample containing the antigen 306, and the labeled antibody 308 may be weighed out into the respective chambers; the magnetic-particle-immobilized antibody 305, the sample containing the antigen 306, and the labeled antibody 308 having been injected into the respective chambers may be transferred to the reaction chamber 102; and they may be mixed in the reaction chamber 102 to form the composite 310. Moreover, the magnetic-particle-immobilized antibody 305 and the labeled antibody 308 may be dried (hereinafter referred to as "dried reagents"). In this case, for example, the dried reagents may be retained in the reaction chamber 102, and dissolved by a liquid containing a sample solution containing the antigen 306 to form the composite 310. Moreover, during measurement, a dried reagent which is retained in a certain chamber that is not the reaction chamber 102 may be dissolved by a liquid, then transferred to the chamber 102, and mixed with the sample containing the antigen 306 in the reaction chamber 102, thereby allowing the composite 310 to form.

The channel 104 has a path that connects the reaction chamber 102 and the measurement chamber 103, with one end being connected to the reaction chamber 102, and the other end being connected to the measurement chamber 103. The position of connection between the reaction chamber 102 and the channel 104 is located closer to the rotation axis 101 than is the position of connection between the measurement chamber 103 and the channel 104. With this construction, the solution containing the composite 310 receives a centrifugal force which is generated by rotation of the sample analysis substrate 100, and is transferred to the measurement chamber 103 via the channel 104.

In the measurement chamber 103, a B/F separation of the solution containing the composite 310 takes place. For this purpose, the sample analysis substrate 100 includes a magnet 106. In the substrate 110, the magnet 106 is located close to the space of the measurement chamber 103.

The magnet 106 is located more distant from the rotation axis 101 than is the measurement chamber 103. The magnet 106 may be capable of attachment and detachment for B/F separation, or undetachably attached to the sample analysis substrate 100. The magnet 106 may be a magnet to be commonly used in an immunoassay technique which involves a competitive assay using magnetism particles, for example. Specifically, a ferrite magnet, a neodymium magnet, or the like may be used. In particular, a neodymium magnet has a strong magnetic force, and is suitably used for the magnet 106.

As shown in FIG. 2A, the channel 105 has a path connecting the measurement chamber 103 and the recovery chamber 107, with one end being connected to the measurement chamber 103, and the other end being connected to the recovery chamber 107. The position of connection between the measurement chamber 103 and the channel 105 is located closer to the rotation axis 101 than is the position of connection between the recovery chamber 107 and the channel 105. With this construction, the liquid which has been separated from the solution containing the composite 310 through B/F separation receives a centrifugal force which is generated by rotation of the sample analysis substrate 100, and is transferred to the recovery chamber 107 via the channel 105.

The spaces of the reaction chamber 102, the measurement chamber 103, and the recovery chamber 107 may be about 10 μl to about 500 μl in size, for example. Preferably, the channel 104 and the channel 105 is composed in a size which allows themselves to be filled with the liquid that is retained in the reaction chamber 102 and the measurement chamber 103 via capillary action. In other words, the channel 104 and the channel 105 are preferably capillary channels or capillary tubes. For example, a cross section which is perpendicular to the direction that each of the channel 104 and the channel 105 extends may have a width of 0.1 mm to 5 mm and a depth of 50 μm to 300 μm, or have a width of 50 μm or more (preferably 50 μm to 300 μm) and a depth of 0.1 mm to 5 mm.

At least one air hole 108 is provided in each of the reaction chamber 102, the measurement chamber 103, and the recovery chamber 107. As a result, the interior of each chamber is maintained at the environmental air pressure, so that the liquid may move through the channel 104 or 105 by capillary action and the siphon principle. Moreover, an opening 109 through which to inject or discharge liquids such as a sample solution, reaction solution, or a wash solution may be made in the reaction chamber 102 and the recovery chamber 107. As used herein, the siphon principle refers to the control on liquid transfer which is based on a balance between a centrifugal force that acts on a liquid due to rotation of the sample analysis substrate 100 and the capillary force within the channel.

(Construction of Sample Analysis Device 200)

Figure 3A:
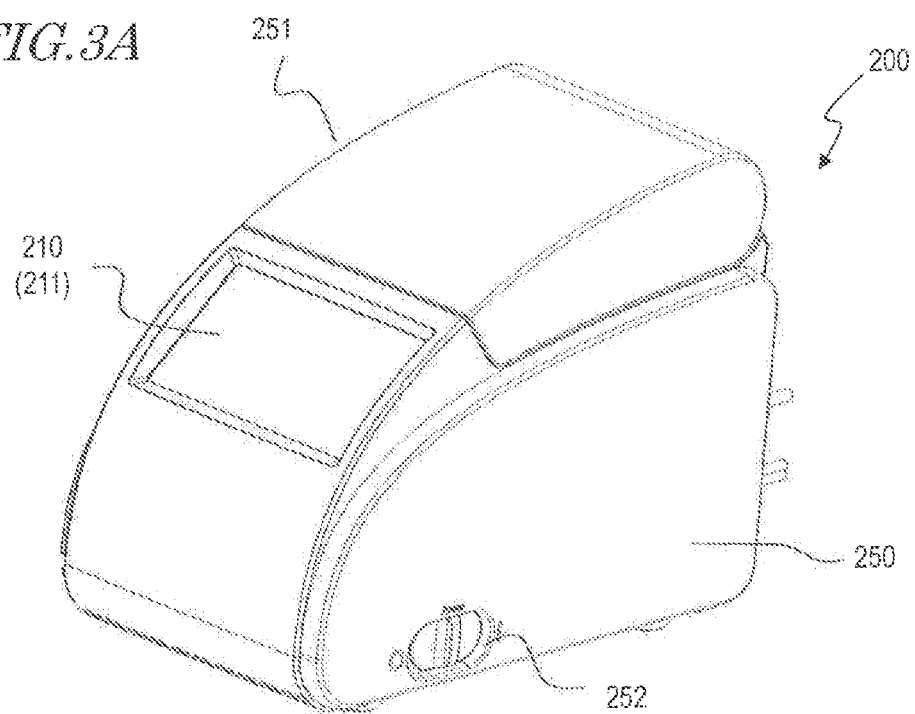
FIG. 3A is a perspective view showing the appearance of a sample analysis device.
Figure 3B:
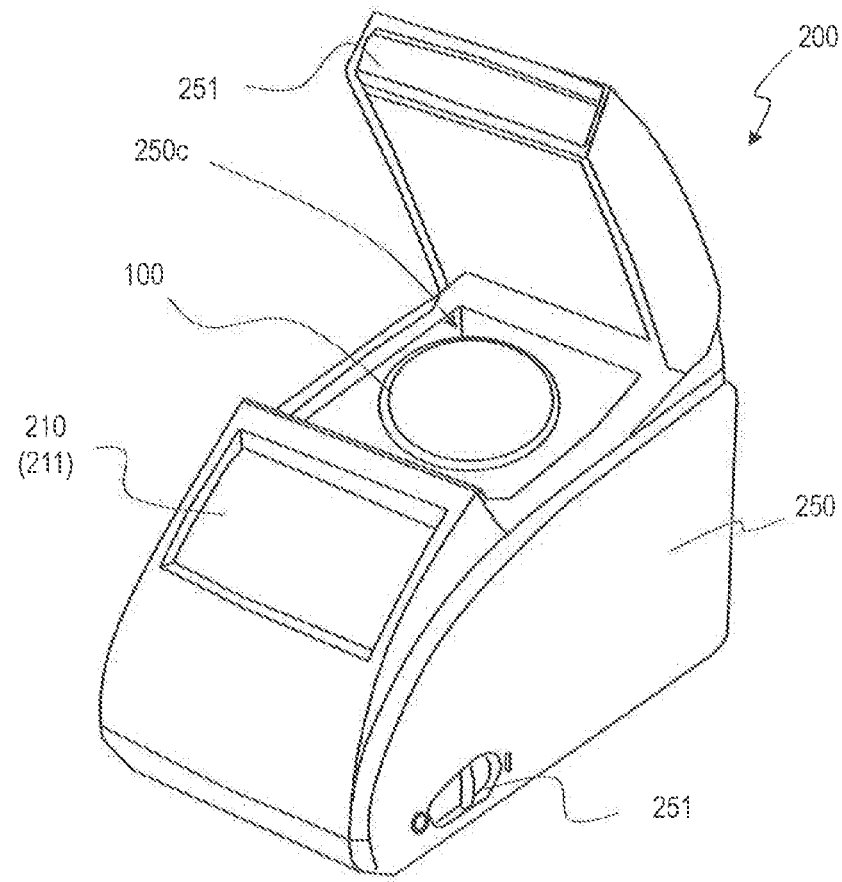
FIG. 3B is a perspective view showing the appearance of a sample analysis device with its door open.
Figure 4A:
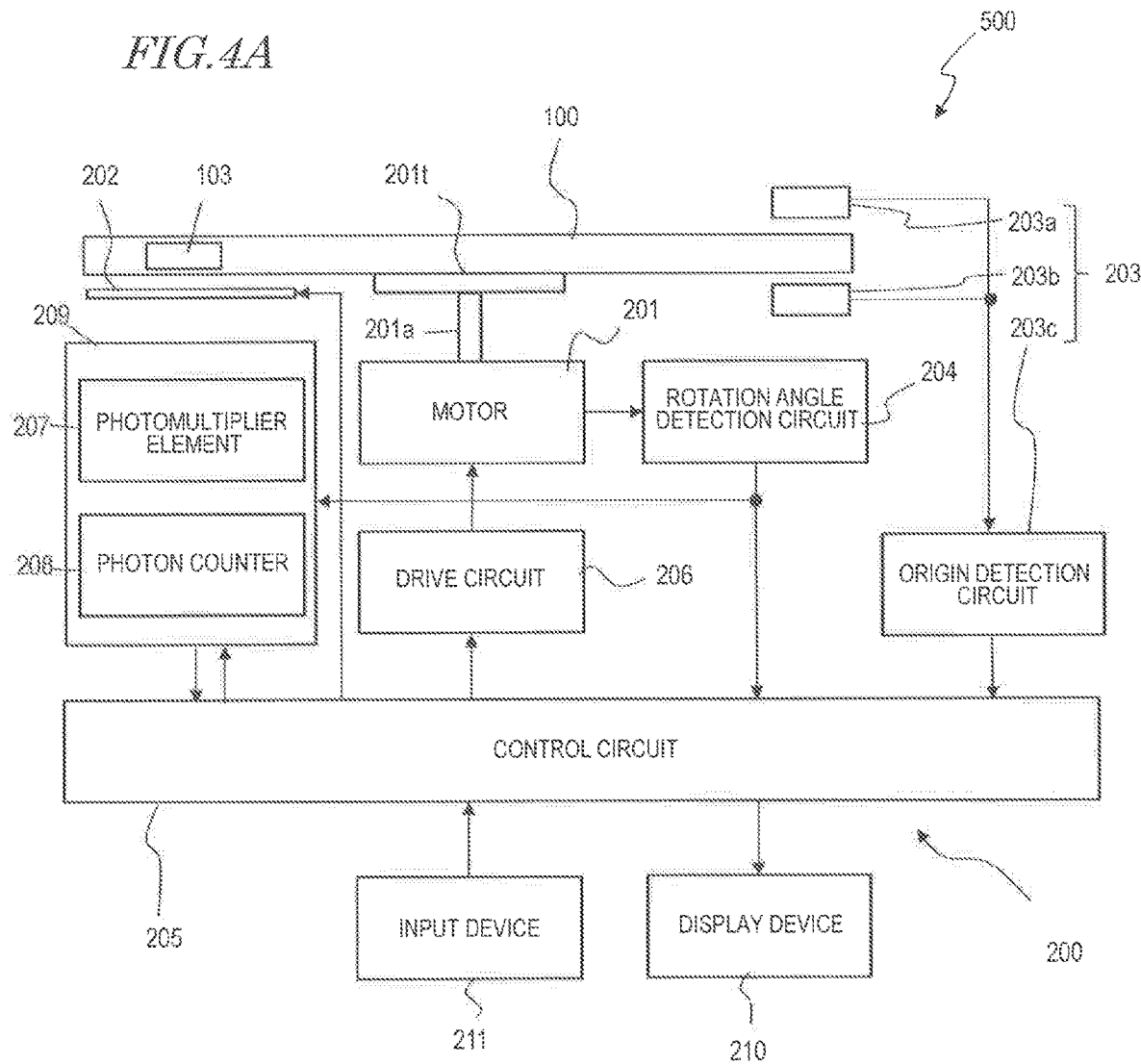
FIG. 4A is a block diagram illustrating an exemplary sample analysis system.

FIG. 3A and FIG. 3B are perspective views showing an exemplary appearance of the sample analysis device 200. FIG. 4A is a block diagram showing an exemplary construction of the sample analysis device 200. The sample analysis device 200 has a housing 250 that includes a door 251 which is capable of opening and closing. The housing 250 has an accommodation 250c in which the sample analysis substrate 100 is accommodated so as to be capable of rotation. In the accommodation 250c, a motor 201 (FIG. 4A) having a turntable 201t is disposed. While the door 251 is open, the sample analysis substrate 100 can be attached to or detached from the turntable 201t within the accommodation 250c. As the door 251 is closed, the door 251 shields the accommodation 250c from light so that no light may enter the accommodation 250c from the exterior. On the housing 250, a power switch 252 for starting or stopping the sample analysis device 200 and a display device 210 (to be described later) are provided.

With reference to FIG. 4A, the sample analysis device 200 will be described in detail. The sample analysis device 200 includes the motor 201, the shutter 202, an origin detector 203, a rotation angle detection circuit 204, a control circuit 205, a drive circuit 206, the photodetector 209, a display device 210, and an input device 211.

The motor 201, which has the turntable 201t supporting the sample analysis substrate 100, and rotates the sample analysis substrate 100 around a shaft 201a. The shaft 201a may be inclined from the direction of gravity at an angle of not less than 0° and not more than 90° with respect to the direction of gravity. The motor 201 may rotate the sample analysis substrate in a range from 100 rpm to 8000 rpm, for example. The rotation speed may be determined in accordance with the shape of each chamber and channel, the physical properties of liquids, the timing of transfers of liquids and treatments, and the like. The motor 201 may be a DC motor, a brushless motor, an ultrasonic motor, or the like, for example.

For example, the origin detector 203 includes a light source 203a, a photodetector 203b, and an origin detection circuit 203c, and is disposed so that the sample analysis substrate 100 comes between the light source 203a and the photodetector 203b. For example, the light source 203a may be a light-emitting diode, and the photodetector 203b may be a photodiode. The light source 203a may be attached on the inside of the door 251, for example.

The origin detector 203 detects an origin of the sample analysis substrate 100 attached to the motor 201. Specifically, the boundary between a light-transmitting portion and a shading portion of the sample analysis substrate 100 as an origin. For example, the light-shield cap 120 may have a transmittance of 10% or less for light exiting from the light source 203a along the thickness direction of the sample analysis substrate 100, and a transmittance of 60% or more at the substrate 110.

As the sample analysis substrate 100 is rotated by the motor 201, the photodetector 203b outputs a detection signal which is in accordance with the amount of incident light on the origin detection circuit 203c. As shown in FIG. 2A, depending on the direction of rotation, the detection signal may increase or decrease at an edge 120e and at an edge 210b of the light-shield cap 120. The origin detection circuit 203c detects a decrease in the amount of detected light and outputs it as an origin signal, for example, while the sample analysis substrate 100 is rotating clockwise as indicated by the arrow. In the present specification, the position of the edge 120e of the light-shield cap 120 will be regarded as the origin position of the sample analysis substrate 100 (i.e., a reference angular position of the sample analysis substrate 100). However, a position at any specific angle, as arbitrarily determined from the position of the edge 120e, might be defined as an origin.

The origin position is utilized by the sample analysis device 200 in acquiring information on the rotation angle of the sample analysis substrate 100. The origin detector 203 may have any other construction. For example, a magnet for use in origin detection may be provided on the sample analysis substrate 100, and, instead of the photodetector 203b, the origin detector 203 may include a magnetism detector which detects magnetism of this magnet. Moreover, the magnet 106 for use in capturing the magnetic particles may also be utilized for origin detection. In the case where the sample analysis substrate 100 is attachable to the turntable 201t only at a specific angle, the origin detector 203 may be omitted.

The rotation angle detection circuit 204 detects the angle of the shaft 201a of the motor 201. For example, the rotation angle detection circuit 204 may be a rotary encoder that is attached to the shaft 201a. In the case where the motor 201 is a brushless motor, the rotation angle detection circuit 204 may include a Hall generator that is provided on the brushless motor and a detection circuit which receives an output signal from the Hall generator and outputs a rotation angle signal representing the angle of the shaft 201a. When the sample analysis substrate 100 is attached to the turntable 201t, the sample analysis substrate 100 rotates around the shaft 201a, and thus the rotation angle detection circuit 204 is able to detect the rotation angle of the sample analysis substrate 100 and output a rotation angle signal. The rotation angle signal may be, for example, a pulse signal containing pulses that are output by every predetermined angle.

The drive circuit 206 drive the motor 201 to rotate. Specifically, based on instructions from the control circuit 205, the sample analysis substrate 100 is rotated clockwise or counterclockwise, and its swings or rotation is stopped.

The photodetector 209 detects luminescence occurring from the label substance 307 of the labeled antibody 308 bound to the composite 310 (FIG. 1) being retained in the measurement chamber 103 of the sample analysis substrate 100. Herein, luminescence refers to any release of photons, irrespective of the principle of luminescence, e.g., fluorescence or phosphorescence. That is, the photodetector 209 measures a number of photons in the luminescence occurring from the label substance 307. Specifically, the photodetector 209 includes a photomultiplier element 207 and a photon counter 208. The photomultiplier element 207 receives photons in the luminescence occurring from the label substance 307, and outputs a number of pulses that is in accordance with the number of photons. With the sample analysis substrate 100 being attached to the turntable 201t, the light-receiving surface of the photomultiplier element 207 is disposed below a concentric circle 103c (FIG. 2A) on which the measurement chamber 103 is located.

Figure 4B:
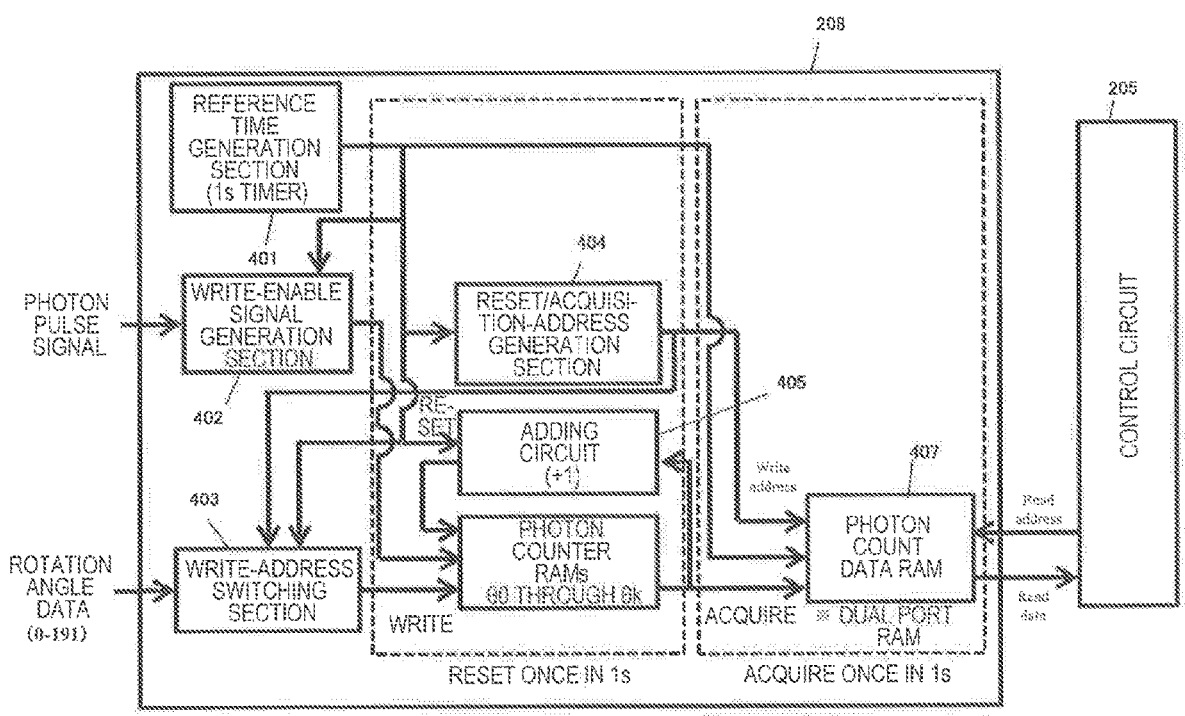
FIG. 4B is a block diagram illustrating an exemplary photon counter according to a first embodiment.

The photon counter 208 measures the number of pulses in the pulse signal which is output from the photomultiplier element 207, based on a predetermined unit of reference. For example, the photon counter 208 has a construction as shown in FIG. 4B, and counts the number of photons based on the rotation angle of the sample analysis substrate 100 as a unit of reference. Specifically, based on a rotation angle signal which is output from the rotation angle detection circuit 204, the photon counter 208 divides the angle of one complete turn, i.e., 360°, of the sample analysis substrate 100 into a plurality of phase ranges θ0 to θk, and measures the number of pulses in accordance with photons, by using counters for the respective phase ranges. Note that k may be 191, for example, and the photon counter 208 may count the number of photons with a resolving power of 1.875°. To this end, the photon counter 208 includes a reference time generation section 401, a write-enable signal generation section 402, a write-address switching section 403, a reset/acquisition-address generation section 404, an adding circuit 405, photon counter RAMs θ0 through θk, and a photon count data RAM 407.

The reference time generation section 401 generates a reference time for resetting the counters. For example, the reference time may be 1 second. The write-enable signal generation section 402 generates a write-enable signal each time receiving a pulse signal based on photons. Based on a rotation angle signal which is output from the rotation angle detection circuit 204, the write-address switching section 403 switches between the photon counter RAMs θ0 through θk to which a write is made.

The reset/acquisition-address generation section 404 generates addresses at which the data of the photon counter RAMs θ0 through θk are to be written to the photon count data RAM 407.

The adding circuit 405 and the photon counter RAMs θ0 through θk constitute (k+1) counters for the phase ranges θ0 to θk.

The photon count data RAM 407, which is a register, reads the count numbers as counted by the photon counter RAMs θ0 through θk, and temporarily stores the count numbers until the control circuit has read the count numbers.

While the photomultiplier element 207 outputs a pulse signal upon detection of photons in the luminescence occurring from the label substance 307, the write-enable signal generation section 402 generates a write-enable signal each time receiving a pulse based on a photon. Since the write-address switching section 403 consecutively switches between the photon counter RAMs θ0 through θk to write to based on the rotation angle signal, the write-enable signal is input to one of the photon counter RAMs θ0 through θk that corresponds to the angle of the sample analysis substrate 100 at the time of a photon occurrence, and the adding circuit 405 causes the count number in that RAM to be incremented by one.

Based on address signals generated by the reset/acquisition-address generation section 404, the photon count data RAM 407 reads the count numbers that are stored in the photon counter RAMs θ0 through θk. The reference time generation section 401 resets these circuits at the lapse of every reference time.

The control circuit 205 reads the values of the photon counter RAMs θ0 through θk as stored into the photon count data RAM 407. As a result, during the course of every reference time as output by the reference time generation section 401, a plurality of measurement values which represent the numbers of photons for the phase ranges θ0 to θk are obtained.

If the time interval of counting the number of photons is sufficiently shorter than the amount time required for one complete turn of the sample analysis substrate 100, the photon counter 208 may count the number of photons on the basis of time. While the sample analysis substrate 100 is rotating with a constant rotation speed, ideally speaking, the rotation speed during one complete turn of the sample analysis substrate 100 is essentially constant, irrespective of the rotation angle. For example, the amount of time required for the sample analysis substrate 100 to rotate by 1° is constant while the rotation angle of the sample analysis substrate 100 ranges from 0° to 359°. Therefore, it is possible to count the number of photons while relying on time as a unit of reference.

The photomultiplier element 207 may be a traditional photomultiplier tube which is based on a vacuum tube having a plurality of electrodes thereon, or a semiconductor-based photomultiplier element, such as a silicon photomultiplier utilizing an avalanche photodiode in Geiger mode. Moreover, the photon counter 208 may be incorporated in the control circuit 205 as described below. The photon counter 208 is composed of an integrated circuit such as an FPGA, for example. Alternatively, the aforementioned signal processing by the photon counter 208 may be carried out by software that is executed by the control circuit 205.

The shutter 202 is provided between the light-receiving surface of the photomultiplier element 207 of the photodetector 209 and the sample analysis substrate 100, and controls opening and closing of the light-receiving surface. While the shutter 202 is open, luminescence occurring from the composite 310 being retained in the measurement chamber 103 of the rotating sample analysis substrate 100 is incident on the photomultiplier element 207. While the shutter 202 is closed, luminescence is blocked. The shutter 202 may have a mechanical structure, or be a liquid crystal shutter or the like.

The control circuit 205 controls the respective component elements such as the photodetector 209, the drive circuit 206, and the shutter 202. Moreover, the control circuit 205 receives from the photodetector 209 measurement values of the number of photons for each of the phase ranges θ0 to θk as measured by the photodetector 209 while the motor 201 rotates the sample analysis substrate 100, and stores them to memory.

Figure 5:
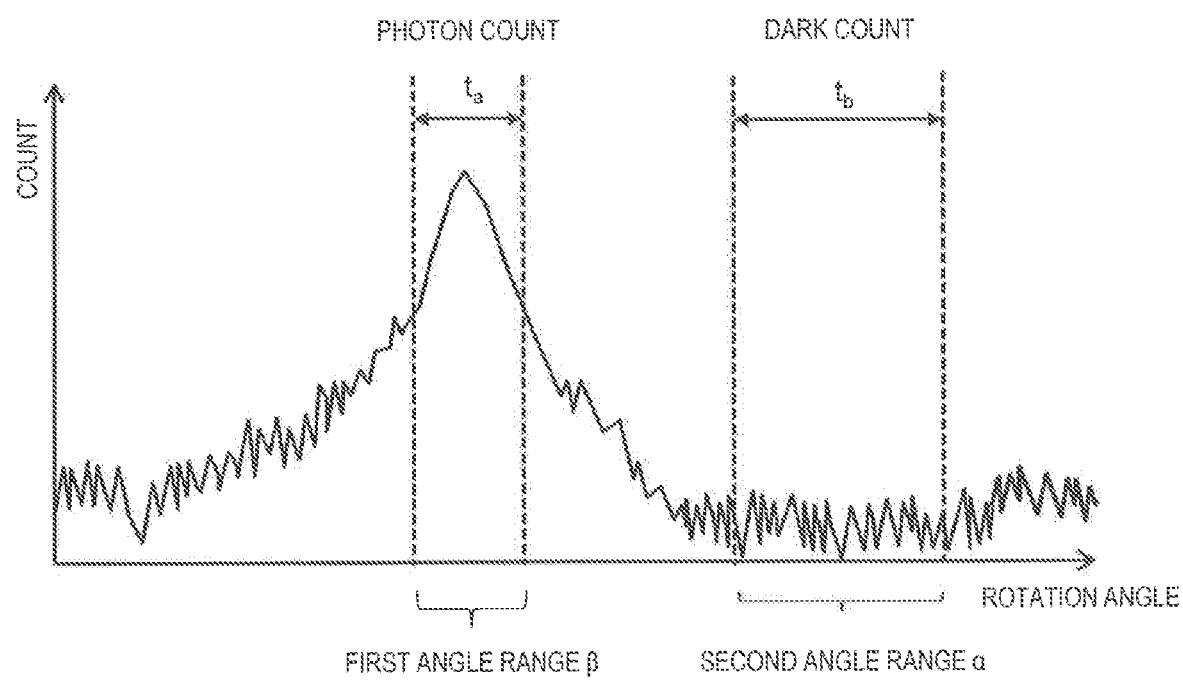
FIG. 5 is a diagram showing an exemplary distribution of numbers of photons to be measured while the sample analysis substrate 100 makes one complete turn.

After measurement is finished, a measurement value of the luminescence of the sample is calculated from a distribution of the numbers of photons for the phase ranges θ0 to θk as stored in the memory, i.e., numbers of photons as a plurality of measurement values that are measured while the sample analysis substrate 100 makes one complete turn. FIG. 5 shows an exemplary distribution of numbers of photons to be measured while the sample analysis substrate 100 makes one complete turn. FIG. 5 shows a distribution of numbers of photons, where 0° on the horizontal axis is based on a point of time at which a position S on the sample analysis substrate 100 passes over the light-receiving surface of the photomultiplier element 207. Since the substrate 110 is light-transmissive, photons are detected even at angles at which the measurement chamber 103 is not passing over the light-receiving surface of the photodetector 209. On the other hand, when the shading portions 120*a* pass over light-receiving surface, hardly any photons are detected.

However, as described above, detection sensitivity of the photomultiplier element 207, particularly in terms of noise, has some temperature dependence. Therefore, even in the case where photons are not actually detected, depending on the measurement temperature, a pulse signal may be output as if a photon were detected. Moreover, other than temperature, there may also be factors that affect accurate measurement of the number of photons. For example, the accommodation 250*c* may not be an ideal darkroom, and light other luminescence occurring from the label substance 307 of the composite 310 may possibly be incident on the photomultiplier element 207.

Therefore, during rotation of the sample analysis substrate 100, the control circuit 205 corrects the number of photons as obtained while detecting the measurement chamber 103, by using the number of photons as obtained while detecting the shading portions 120*a*. Hereinafter, the number of photons as obtained while detecting the measurement chamber 103 will be referred to as a photon count, and the number of photons as obtained while detecting the shading portions 120*a* will be referred to as a dark count.

Specifically, first, within a distribution of numbers of photons as counted during one complete turn of the sample analysis substrate 100, positions of photon counts and dark counts are identified. The positions of photon counts and dark counts can be identified by using the central angle β of the region where the measurement chamber 103 is located and the central angle α of the region where the shading portions 120*a* are located, how many divided phase ranges θ0 to θk there are, and an origin which is detected by the origin detector 203. The photon counts and dark counts within the distribution of numbers of photons as counted during one complete turn of the sample analysis substrate 100 are defined as spanning a first angle range β and a second angle range α, respectively.

Next, from the first angle range β and the second angle range α, a photon count, i.e., at least one first measurement value that is output from the photodetector 209, and a dark count, i.e., at least one second measurement value that is output from the photodetector 209, are determined, and the at least one first measurement value is corrected with the at least one second measurement value.

For example, by subtracting the second measurement value from the first measurement value, a measurement value of luminescence occurring from the composite 310 may be obtained. In more general terms, a measurement value C[s−1] of luminescence occurring from the composite 310 (sample) is expressed by the following Expression (1), where ta[s] is the period corresponding to the first angle range β; tb[s] is the period corresponding to the second angle range α; and, given n and m points of measurement in the respective periods, the number of photons in the respective points of measurement are represented as first measurement values Ai (i=1 to n) and second measurement values Bj (j=1 to m). In other words, the dark count is subtracted from the photon count per unit time, thereby obtaining a measurement value C.

$$C = \frac{1}{t_a}\sum_{i=1}^{n} A_i - \frac{1}{t_b}\sum_{j=1}^{m} B_j \quad (1)$$

In the case where the temperature change over time in the accommodation 250*c* is large, or, when as accurate a correction needs to be made as possible, it is preferable to use photon and dark counts (Ai and Bj) obtained while the sample analysis substrate 100 makes one complete turn. However, in the case where the temperature change over time in the accommodation 250c is not large, or from any other reason, the photon and dark counts may be data that is obtained from a different rotation. Note that a measurement value C of luminescence of the sample as obtained from Expression (1) is a value that is derived through a single rotation. A total of measurement values C obtained through a plurality of rotations may be obtained, or an average of measurement values C obtained through a plurality of rotations may be taken.

Also, by setting a larger second angle range α corresponding to dark counts than the first angle range β corresponding to photon counts, it is possible to prolong the period corresponding to dark counts, which are susceptible to fluctuations, so that more stable dark count values can be obtained. To do this, as mentioned earlier, the central angle α of the region where the shading portions 120a are located may be made greater than the central angle β of the region where the measurement chamber 103 is located.

Through such computation, it is possible to count the number of photons with reduced temperature influences. In particular, by using detection results for the measurement chamber 103 and detection results for the shading portions 120a which are obtained during one complete turn, the number of photons from luminescence and the number of photons from non-luminescence can be measured essentially concurrently, thereby further reducing the influences of temperature changes over time.

The control circuit 205 outputs the measurement value C which has been obtained through this computation to the display device 210. The measurement value C may be allowed to be stored to memory in the control circuit 205.

For example, the control circuit 205 includes a CPU and a memory provided in the sample analysis device 200, as well as an interface with which to receive signals from the origin detector 203, the rotation angle detection circuit 204, and the photodetector 209. By executing a computer program that is loaded into a memory such as an RAM (Random Access Memory), the control circuit 205 sends instructions to other circuitry in accordance with the procedure defined by the computer program. Upon receiving such an instruction, each circuit operates as will be described in the present specification, whereby the function of the respective circuit is realized. The instructions from the control circuit 205 are sent to the drive circuit 206, the shutter 202, and the like, as shown in FIG. 4A, for example. The procedure defined by the computer program is shown by a flowchart described below.

Note that the memory into which a computer program is loaded, e.g., a RAM storing a computer program, may be volatile or non-volatile. A volatile RAM is a RAM which in the absence of supplied power is unable to retain the information that is stored therein. For example, a dynamic random access memory (DRAM) is a typical volatile RAM. A non-volatile RAM is a RAM which is able to retain information without power being supplied thereto. For example, a magnetoresistive RAM (MRAM), a resistive random access memory (ReRAM), and a ferroelectric memory (FeRAM) are examples of non-volatile RAMs. In the present embodiment, a non-volatile RAM is preferably adopted. A volatile RAM and a non-volatile RAM are both examples of non-transitory, computer-readable storage media. Moreover, a magnetic storage medium such as a hard disk, and an optical storage medium such as an optical disc are also examples of non-transitory, computer-readable storage media. That is, a computer program according to the present disclosure may be recorded on various non-transitory computer-readable media, excluding any medium such as the atmospheric air (transitory media) that allows a computer program to be propagated as a radiowave signal.

In the present specification, the photon counter 208 of the photodetector 209 and the control circuit 205 are described as distinct component elements from the rotation angle detection circuit 204 and the origin detection circuit 203c of the origin detector 203. However, these may be implemented by the same hardware. For example, in a serial or parallel manner, a CPU (computer) which is provided in the sample analysis device 200 may execute a computer program to function as the photon counter 208, a computer program to function as the control circuit 205, a computer program to function as the rotation angle detection circuit 204, and a computer program to function as the origin detection circuit 203c of the origin detector 203. This allows the CPU to apparently operate as distinct component elements.

The display device 210 is a display panel such as a liquid crystal display panel or an organic EL panel, and displays: the aforementioned measurement value C which is output from the control circuit 205 and/or information based on the measurement value C; a past measurement value(s) C; information for prompting the operator to make inputs as part of the manipulation of the sample analysis device 200; and so on.

Based on the operator's manipulation, the input device 211 gives an instruction to the control circuit 205. The input device 211 may be a touch screen panel that is provided on the display device 210, for example.

(Operation of Sample Analysis System)

Figure 6:
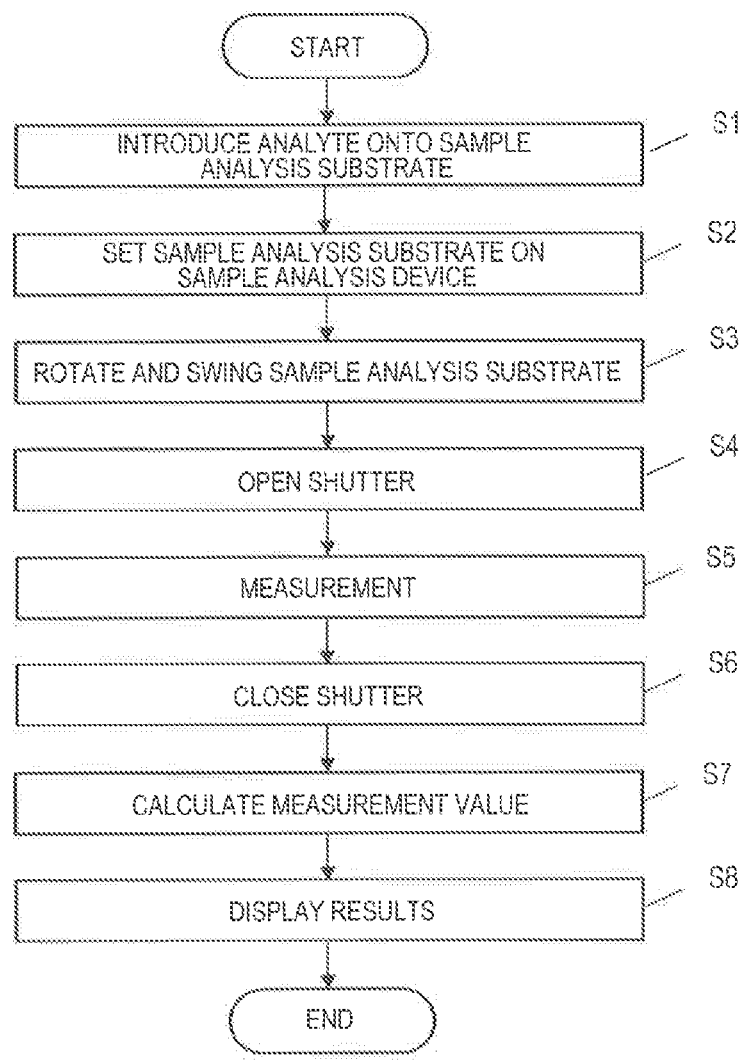
FIG. 6 is a flowchart showing an exemplary operation of a sample analysis system.

With reference to FIG. 1, FIG. 2A, FIG. 4A, FIG. 4B, FIG. 5, and FIG. 6, an operation of a sample analysis system 500 will be described. FIG. 6 is a flowchart showing an operation of the sample analysis system 500.

(1) A Process of Introducing a Sample on the Sample Analysis Substrate

[Step S1]

First, in the reaction chamber 102 of the sample analysis substrate 100, the magnetic-particle-immobilized antibody 305, a sample containing the antigen 306, and the labeled antibody 308 are allowed to react simultaneously, thereby forming the composite 310. For example, a liquid containing the magnetic-particle-immobilized antibody 305 may be retained in the reaction chamber 102, and a sample containing the antigen 306 and a liquid containing the labeled antibody 308 may be introduced through the opening 109 into the reaction chamber 102, with a syringe or the like. In the case where a chamber (not shown) retaining the sample containing the antigen 306 and the labeled antibody 308 is provided in the sample analysis substrate 100, the sample may be introduce into that chamber. The labeled antibody 308 may have been introduced into the chamber in advance.

[Step S2]

The power switch 252 of the sample analysis device 200 is turned ON. The door 251 of the sample analysis device 200 is opened, and the sample analysis substrate 100 is attached to the turntable 201t. The door 251 is closed.

(2) A Process of Transferring the Sample to the Measurement Chamber

[Step S3]

In accordance with information which is displayed on the display device 210, as the operator touches on the display device 210, an instruction is input from the input device 211 to the control circuit 205, whereby the sample analysis device 200 operates. First, the motor 201 rotates, and the origin detector 203 detects an origin of sample analysis substrate 100. By using the detected origin position, the motor 201 rotates in a manner of swinging the sample analysis substrate 100, whereby an antigen-antibody reaction takes place in the reaction chamber 102. In the reaction chamber 102, after the composite 310 has occurred, the sample analysis substrate 100 is rotated, thus allowing the solution containing the composite 310 and the unreacted magnetic-particle-immobilized antibody 305 to move to the measurement chamber 103.

After all of the solution containing the composite 310 has been transferred to the measurement chamber 103, the sample analysis substrate 100 is stopped at a predetermined rotation angle. Once the liquid containing the composite 310 and the unreacted magnetic-particle-immobilized antibody 305 is transferred from the reaction chamber 102 to the measurement chamber 103, the composite 310 and the unreacted magnetic-particle-immobilized antibody 305 (hereinafter, a combination of both of these may be referred to merely as "magnetic particles 311") are attracted toward the side face of the measurement chamber 103 by the magnetic force of the magnet 106 and retained there.

Next, as the sample analysis substrate 100 is rotated, a centrifugal force is generated with the rotation, which acts on the liquid in the measurement chamber 103 and the magnetic particles 311 containing the composite 310. The direction of this centrifugal force coincides with the direction of the attractive force that the magnetic particles 311 receive from the magnet 106. As a result, the magnetic particles 311 are strongly pressed against the side face of the measurement chamber 103.

The liquid under the centrifugal force is discharged through the channel 105, and transferred to the recovery chamber 107. Since the magnetic particles 311 are being strongly pressed against the side face of the measurement chamber 103 with a sum of the centrifugal force and the attractive force of the magnet 106, only the liquid is discharged through the channel 105, while the magnetic particles 311 remain in the measurement chamber 103.

After all liquid has moved to the recovery chamber 107, rotation of the sample analysis substrate 100 is stopped. Thus, B/F separation is completed, whereby the liquid and the magnetic particles 311 in the measurement chamber 103 have been separated.

(3) A Process of Measuring Number of Photons from Luminescence

[Step S4]

The shutter 202 is opened, and the sample analysis substrate 100 is rotated. The shutter 202 may be opened only after the rotating sample analysis substrate 100 has attained constant rotation.

[Step S5]

By using the photodetector 209, luminescence occurring from the label substance 307 of the labeled antibody 308 bound to the composite 310, being contained in magnetic particles 311, is detected. Specifically, the photomultiplier element 207 of the photodetector 209 generates a pulse signal in accordance with photons from luminescence; and, by using a rotation angle signal which is output from the rotation angle detection circuit 204, the photon counter 208 counts the number of photons for each of phase ranges θ0 to θk. The control circuit 205 consecutively receives respective measurement values for the phase ranges θ0 to θk, and stores them to memory.

[Step S6]

After detecting luminescence for a certain period of time, the shutter 202 is closed, and detection is ended.

(4) A Process of Correcting Measurement Values

[Step S7]

From the memory, the control circuit 205 reads out respective measurement values for the phase ranges θ0 to θk, and after determining a period corresponding to photon counting and a period corresponding to dark counting as described above, determines a measurement value C in accordance with Expression (1), for example.

(5) A Process of Displaying Measurement Value

[Step S8]

On the display device 210, the measurement value C and/or index values concerning the amount, concentration, etc., of antigen as determined from the measurement value C.

(Effects)

With the sample analysis device, sample analysis system, and method of measuring luminescence according to the present embodiment, luminescence of a sample is measured while rotating a sample analysis substrate that has a shading portion(s). As a result, a photodetector is able to acquire a measurement value from luminescence of the sample, and also a measurement value of a state where the photodetector is shaded. Moreover, the measurement value from luminescence of the sample can be corrected with the shaded measurement value, thereby suppressing influences of fluctuations in the measurement value due to temperature changes in the photodetector and/or any stray light or the like which is not luminescence of the sample during measurement, thus enabling highly accurate measurement. In particular, since the measurement from luminescence of the sample and the shaded measurement can be acquired during rotation of the sample analysis substrate, e.g., during one complete turn, the time interval between the two measurements can be made short. This reduces the change, if any, in the temperature of the measuremental environment between the two measurements, thus permitting a highly accurate temperature compensation for the measurement value.

(Variants)

Figure 7:
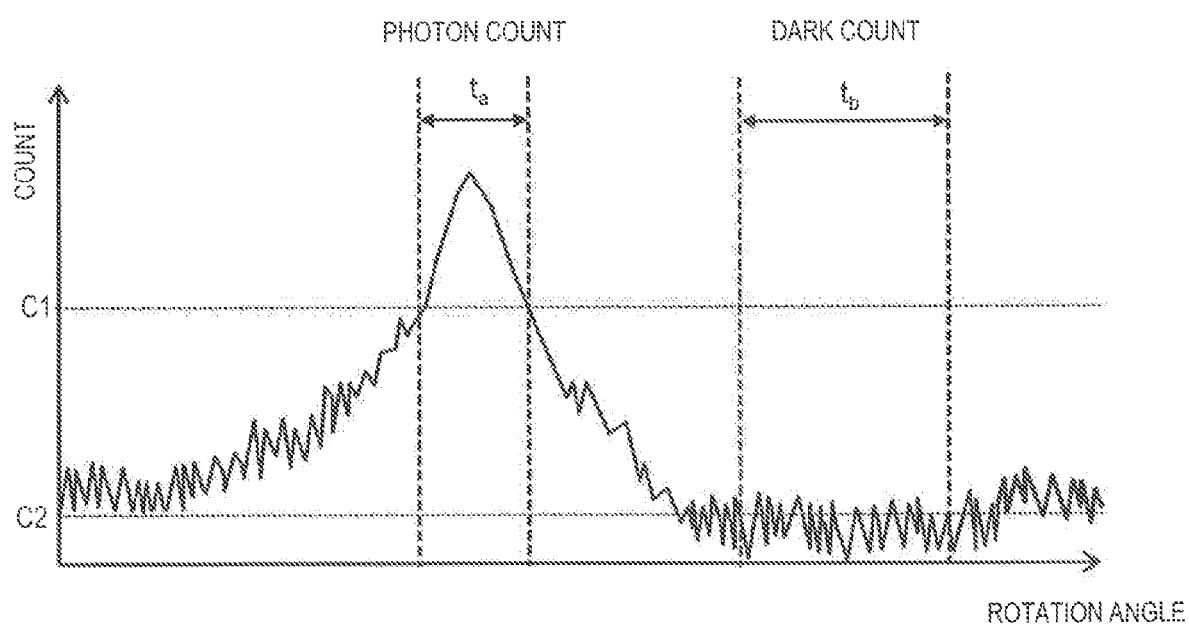
FIG. 7 is a diagram showing another method of determining photon counts and dark counts.

The sample analysis device, sample analysis system, and method of measuring luminescence according to the present disclosure admits of various modifications. For example, although the sample analysis device 200 of the above embodiment includes the rotation angle detection circuit 204, luminescence measurement may instead be made without using a rotation angle signal that is obtained from the rotation angle detection circuit 204. In this case, similarly to a generic photon counter, the photon counter 208 may count the pulses which are output from the photomultiplier element 207 over the course of a predetermined reference time, and output them to the control circuit 205. The control circuit 205 may store a first threshold C1 and a second threshold C2 in memory, such that the first threshold C1 is greater than the second threshold C2 (C1>C2). As shown in FIG. 7, the rotation angle signal may be compared against each of the first threshold C1 and the second threshold C2, and any measurement value that is equal to or greater than the first threshold C1 may be determined to be a first measurement value as obtained while detecting the measurement chamber 103, i.e., a photon count, and any measurement value that is equal to or less than the second threshold C2 may be determined to be a second measurement value, i.e., a dark count. Thereafter, the resultant first measurement value may be corrected with the second measurement value to obtain a measurement value C. In this case, due to noise and other influences, the dark count may in some cases be likely to exceed the second threshold, even though the shading portions 120a are being detected. Therefore, if three or fewer consecutive measurement values have exceeded the second threshold, for example, they may be determined to be second measurement values.

Moreover, the signal representing the number of photons may be utilized in monitoring the operation of the sample analysis device. For example, in the sample analysis substrate 100, in order to detect luminescence of a sample, the sample to undergo luminescence is accommodated in the measurement chamber 103. However, due to inappropriate transfer of the sample, some composite 310 may be left in the reaction chamber 102, or transferred to the recovery chamber 107 without being captured by the magnet 106. In this case, since the amount of composite 310 accommodated in the measurement chamber 103 is reduced, proper measurement may not be possible.

Figure 8:
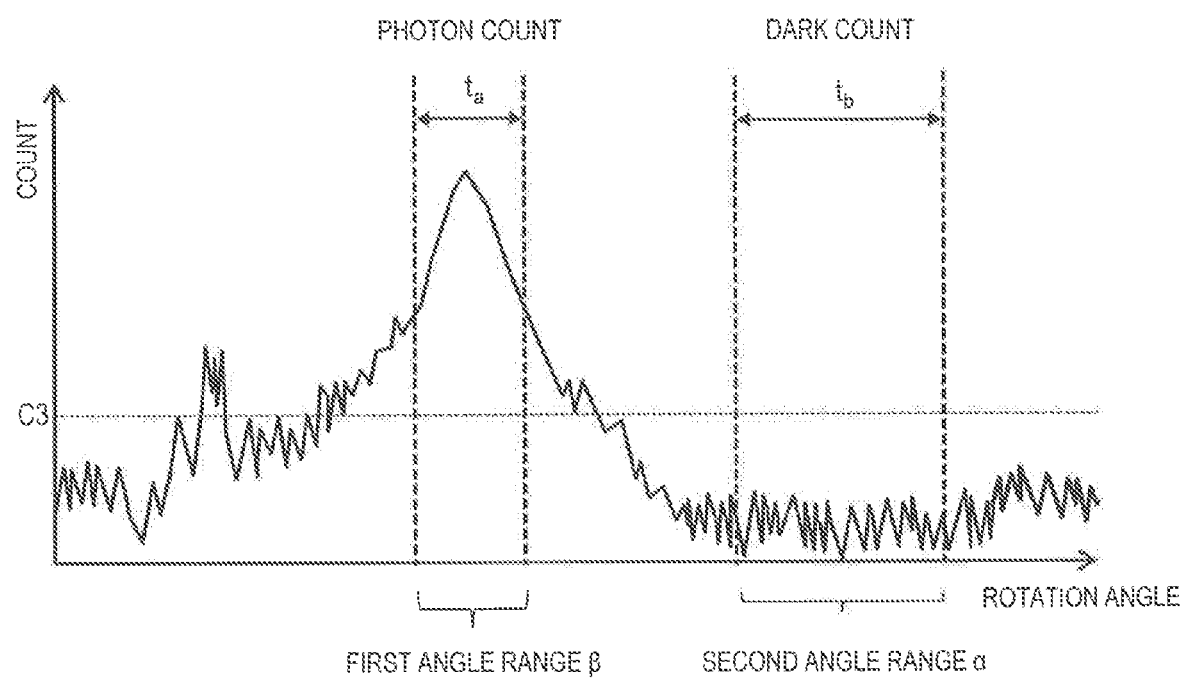
FIG. 8 is a diagram showing a method of detecting abnormalities of a sample analysis device by using a distribution of numbers of photons.

FIG. 8 shows, in a case where some of the composite 310 undergoing luminescence is left in the reaction chamber 102, or has been transferred to the recovery chamber 107, an exemplary distribution of numbers of photons to be counted while the sample analysis substrate 100 makes one complete turn. As shown in FIG. 8, even when the rotation angle is not in the first angle range, luminescence by the composite 310 located in the reaction chamber 102 and/or the recovery chamber 107 is being detected. Therefore, by detecting this luminescence, the control circuit 205 is able to detect abnormal transfers of the composite 310. Specifically, the control circuit 205 may store a third threshold C3 in memory. The control circuit 205 may compare the signal representing the number of photons against the third threshold C3, and if the signal representing the number of photons is equal to or greater than the third threshold at any rotation angle other than the first angle range, generate a signal indicating a measurement error. When a signal indicating a measurement error is generated, for example, the control circuit 205 may display text, figures, etc., that is indicative of abnormal measurement on the display device 210.

This allows the operator of the sample analysis device 200 to recognize that proper measurement has not been made, and take an appropriate measure, e.g., exchanging the sample analysis substrate to again perform measurement.

Figure 9:
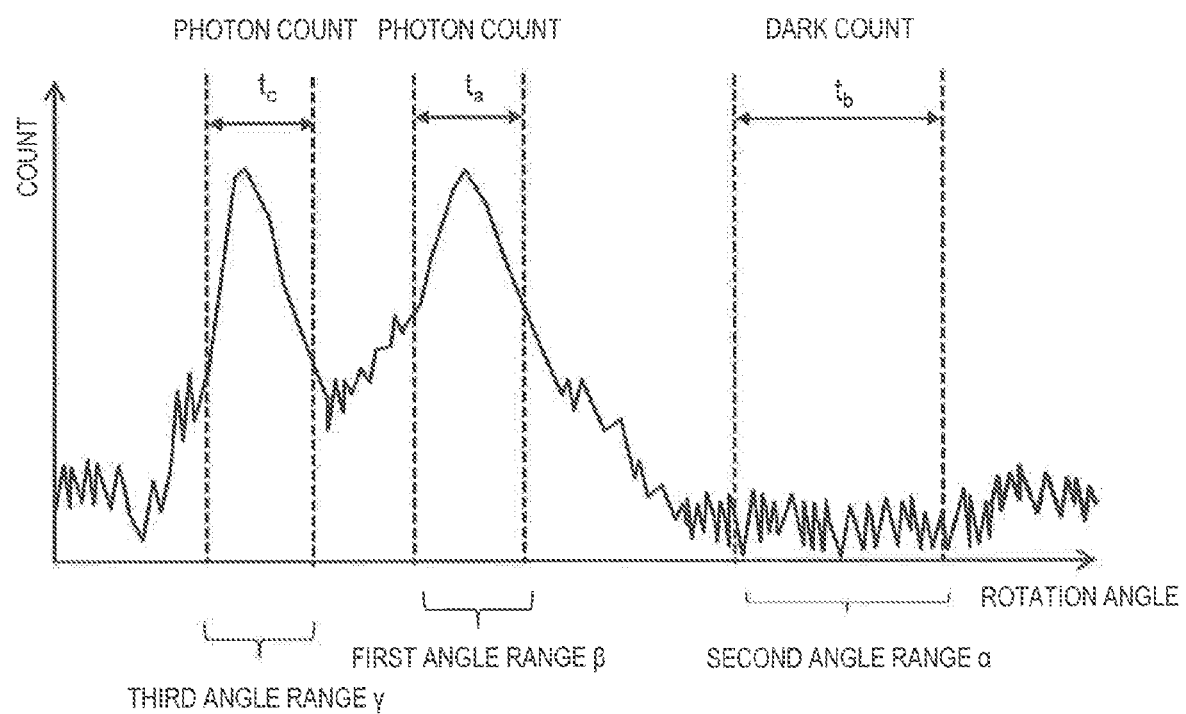
FIG. 9 is a diagram showing an exemplary distribution of numbers of photons in a sample analysis substrate having two measurement chambers.

Moreover, the sample analysis substrate 100 may include two or more measurement chambers 103. FIG. 9 shows, in a case where some of the composite 310 undergoing luminescence is left in the reaction chamber 102, or has been transferred to the recovery chamber 107, an exemplary distribution of numbers of photons to be counted while the sample analysis substrate 100 makes one complete turn.

From a third angle range γ which is based on luminescence from the second measurement chamber 103, the control circuit 205 determines a photon count, i.e., at least one third measurement value to be output by the photodetector 209, and corrects the third measurement value with a dark count, i.e., a second measurement value. As a result, even in the case where the sample analysis substrate includes a plurality of measurement chambers, it is possible to measure luminescence of a sample, which is situated in two measurement chambers, through a single measurement.

Although the above embodiment illustrates that the sample analysis system employs a method of analysis utilizing magnetic particles, luminescence of the sample or a label substance that has bound to the sample may be detected without even using magnetic particles and without performing B/F separation. In this case, the sample analysis substrate 100 may not have a magnet.

Second Embodiment

In the first embodiment, the rotation speed is assumed to be essentially constant during one complete turn of the sample analysis substrate 100, irrespective of the rotation angle; and a subtle amount of luminescence is measured by using a photon counter. However, when luminescence of a sample is measured by a photon counter while the sample analysis substrate is being rotated, due to the mechanical tolerance of the motor, eccentricity of the center of gravity due to the structure of the sample analysis substrate, etc., the angular velocity may vary from angle to angle while the sample analysis substrate makes one complete turn. If such changes in angular velocity occur during one complete turn, the time of measurement for counting photons, as based on angle, may vary. This may make it difficult to make accurate measurements of the number of photons. In the present embodiment, in order to enable accurate measurements of the number of photons even in such cases, the photon counter 208 makes corrections such that the counting time for the number of photons per unit rotation angle of the sample analysis substrate is equal.

Figure 10:
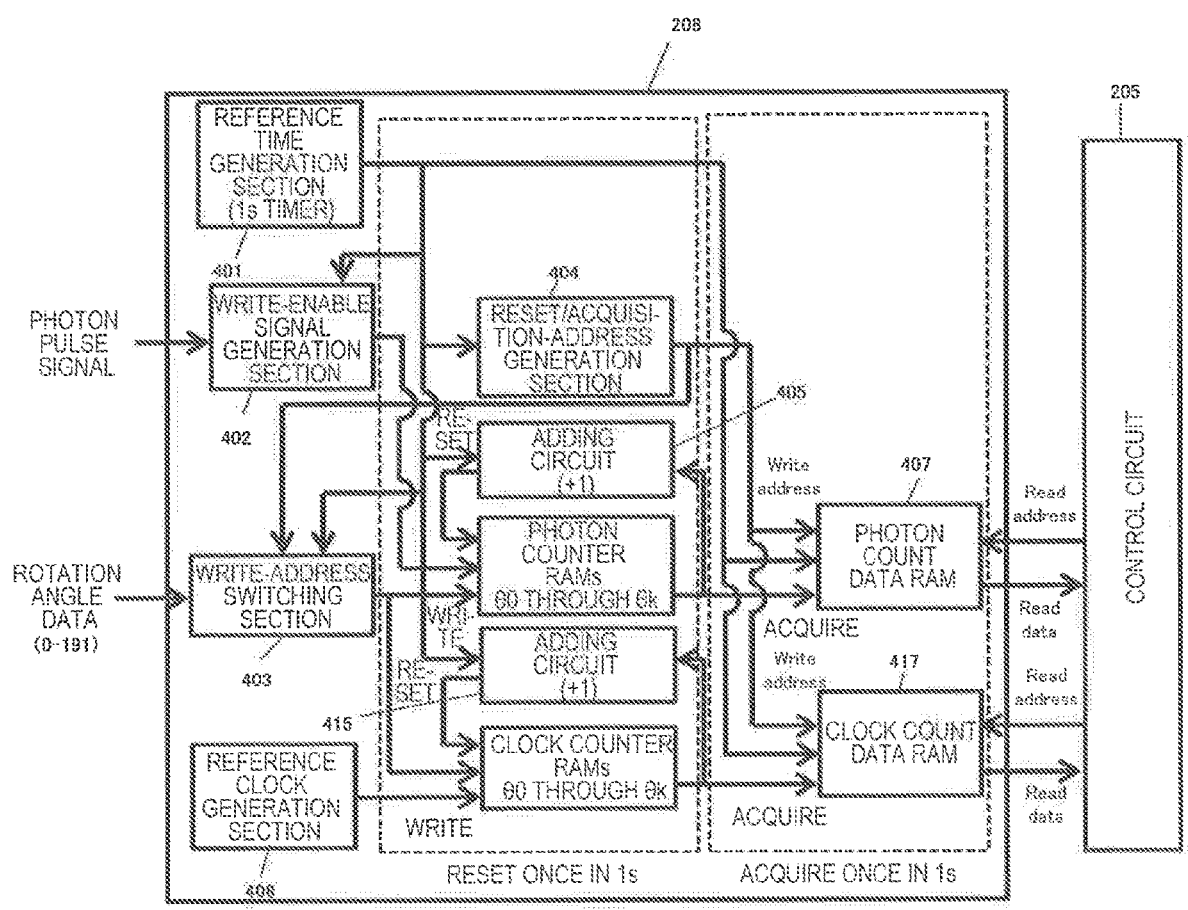
FIG. 10 is a block diagram showing an exemplary photon counter according to a second embodiment.

FIG. 10 is a diagram showing an exemplary construction of the photon counter 208 according to the present embodiment. The photon counter 208 measures the number of pulses in a pulse signal which is output from the photomultiplier element 207, based on a predetermined unit of reference. For example, the photon counter 208 may count the number of photons based on the rotation angle of the sample analysis substrate 100 as a unit of reference. Moreover, the photon counter 208 counts the number of pulses of a reference clock signal based on the rotation angle of the sample analysis substrate 100 as a unit of reference. Specifically, based on a rotation angle signal which is output from the rotation angle detection circuit 204, the photon counter 208 divides the angle of one complete turn, i.e., 360°, of the sample analysis substrate 100 into a plurality of phase ranges θ0 to θk, and measures the number of pulses in accordance with photons, by using counters for the respective phase ranges. Note that k may be 191, for example, and the photon counter 208 may count the number of photons with a resolving power of 1.875°. Moreover, based on a rotation angle signal which is output from the rotation angle detection circuit 204, the angle of one complete turn, i.e., 360°, of the sample analysis substrate 100 is divided into a plurality of phase ranges θ0 to θk, and the number of pulses in a reference clock signal is measured by using counters for the respective phase ranges.

To this end, the photon counter 208 includes a reference time generation section 401, a write-enable signal generation section 402, a write-address switching section 403, a reset/acquisition-address generation section 404, an adding circuit 405, photon counter RAMs θ0 through θk, a photon count data RAM 407, a reference clock generation section 408, an adding circuit 415, clock counter RAMs θ0 through θk, and a clock count data RAM 417.

The reference time generation section 401 generates a reference time for resetting the counters. For example, the reference time may be 1 second. The write-enable signal generation section 402 generates a write-enable signal each time receiving a pulse signal based on a photon. Based on a rotation angle signal which is output from the rotation angle detection circuit 204, the write-address switching section 403 switches between the photon counter RAMs θ0 through θk and clock counter RAMs θ0 through θk to which a write is made.

The reset/acquisition-address generation section 404 generates addresses at which the data of the photon counter RAMs θ0 through θk are to be written to the photon count data RAM 407, and addresses at which the data of the clock counter RAMs θ0 through θk are to be written to the clock count data RAM 417.

The adding circuit 405 and the photon counter RAMs θ0 through θk constitute (k+1) counters to count the numbers of photons for the phase ranges θ0 to θk.

The photon count data RAM 407, which is a register, reads the count numbers as counted by the photon counter RAMs θ0 through θk, and temporarily stores the count numbers until the control circuit has read the count numbers.

The reference clock generation section 408 generates a reference clock signal for measuring a length of time for each of the phase ranges θ0 to θk. The reference clock signal includes pulses which are generated at predetermined time intervals. The frequency of the reference clock signal may be e.g. several dozen to several hundred kHz.

The adding circuit 415 and the clock counter RAMs θ0 through θk constitute (k+1) counters to count the number of pulses in the reference clock signal for the phase ranges θ0 to θk.

The clock count data RAM 417, which is a register, reads the count numbers as counted by the clock counter RAMs θ0 through θk, and temporarily stores the count numbers until the control circuit has read the count numbers.

While the photomultiplier element 207 outputs a pulse signal upon detection of photons in the luminescence occurring from the label substance 307, the write-enable signal generation section 402 generates a write-enable signal each time receiving a pulse based on a photon. Since the write-address switching section 403 consecutively switches between the photon counter RAMs θ0 through θk to write to based on the rotation angle signal, the write-enable signal is input to one of the photon counter RAMs θ0 through θk that corresponds to the angle of the sample analysis substrate 100 at the time of a photon occurrence, and the adding circuit 405 causes the count number in that RAM to be incremented by one.

Based on address signals generated by the reset/acquisition-address generation section 404, the photon count data RAM 407 reads the count numbers that are stored in the photon counter RAMs θ0 through θk.

At the same timing as the aforementioned photon measurements, the length of time of each of the phase ranges θ0 to θk is counted. Since the write-address switching section 403 consecutively switches between the clock counter RAMs θ0 through θk to write to based on the rotation angle signal, the reference clock signal which is output from the reference clock generation section is input to one of the clock counter RAMs θ0 through θk that corresponds to the angle of the sample analysis substrate 100 at the time of a photon occurrence, and the adding circuit 415 causes the count number in that RAM to be incremented by one.

Based on address signals generated by the reset/acquisition-address generation section 404, the clock count data RAM 417 reads the count numbers that are stored in the clock counter RAMs θ0 through θk. The reference time generation section 401 resets these circuits at the lapse of every reference time.

The photomultiplier element 207 may be a traditional photomultiplier tube which is based on a vacuum tube having a plurality of electrodes thereon, or a semiconductor-based photomultiplier element, such as a silicon photomultiplier utilizing an avalanche photodiode in Geiger mode. The photon counter 208 is composed of an integrated circuit such as an FPGA, for example. Moreover, the photon counter 208 may be incorporated in the control circuit 205 as described below. Alternatively, the aforementioned signal processing by the photon counter 208 may be carried out by software that is executed by the control circuit 205. The shutter 202 is provided between the light-receiving surface of the photomultiplier element 207 of the photodetector 209 and the sample analysis substrate 100, and controls opening and closing of the light-receiving surface. While the shutter 202 is open, luminescence occurring from the composite 310 being retained in the measurement chamber 103 of the rotating sample analysis substrate 100 is incident on the photomultiplier element 207. While the shutter 202 is closed, luminescence is blocked. The shutter 202 may have a mechanical structure, or be a liquid crystal shutter or the like.

The control circuit 205 controls the respective component elements such as the photodetector 209, the drive circuit 206, and the shutter 202. Moreover, the control circuit 205 receives from the photodetector 209 measurement values of the number of photons for each of the phase ranges θ0 to θk as measured by the photodetector 209 while the motor 201 rotates the sample analysis substrate 100, as well as measurement values of the number of pulses of the reference clock, and stores them to memory.

Figure 11A:
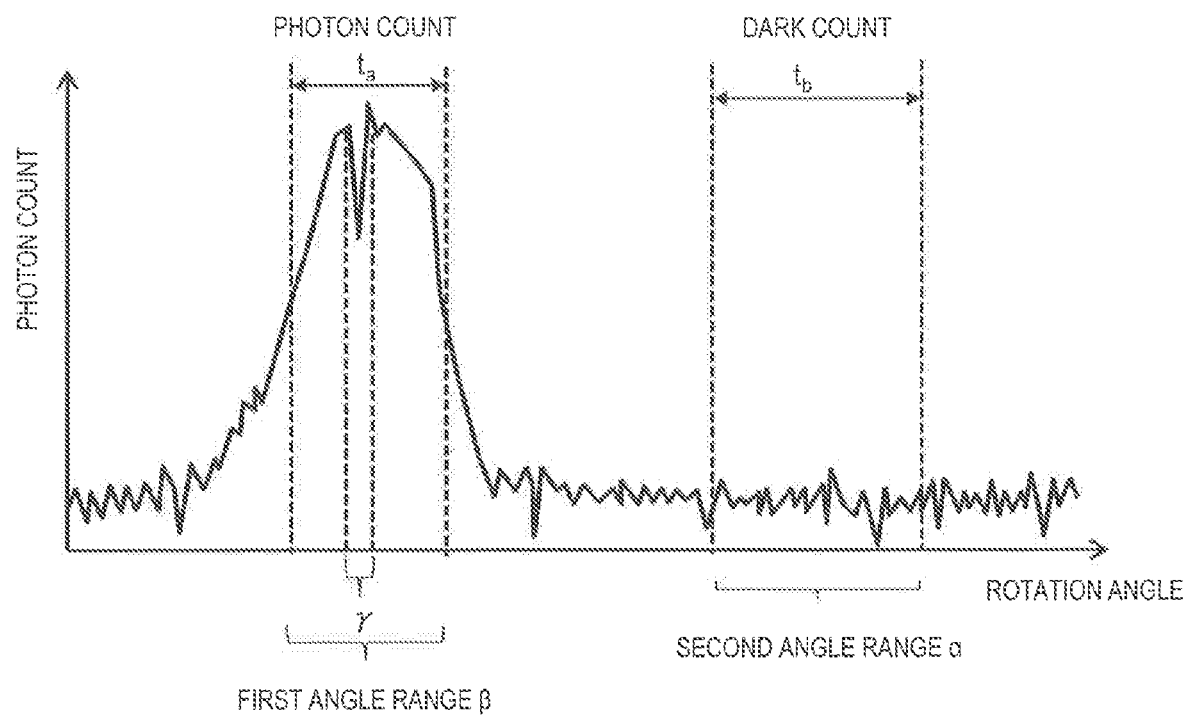
FIG. 11A is a diagram showing an exemplary photon count distribution across rotation angles in the range from 0° to 359°.
Figure 11B:
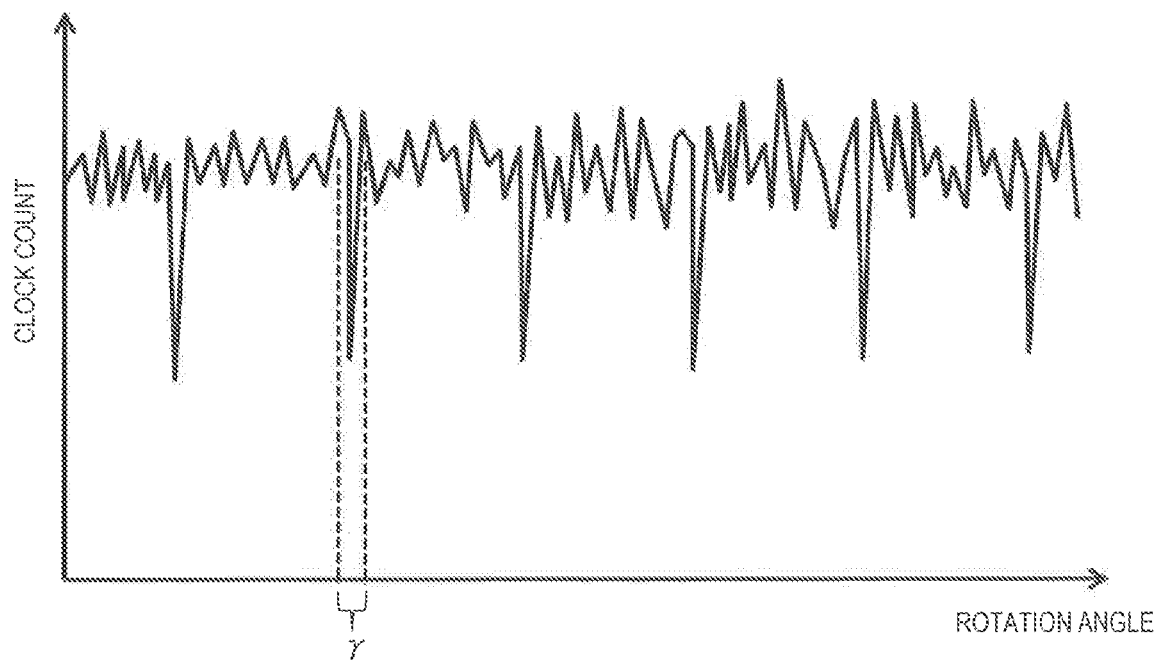
FIG. 11B is a diagram showing an exemplary clock count distribution across rotation angles in the range from 0° to 359°.

FIG. 11A and FIG. 11B show an exemplary photon count distribution and an exemplary clock count distribution in the phase ranges θ0 to θk. As shown in FIG. 11A, in the first angle range β in which the measurement chamber 103 is close to the light-receiving surface of the photomultiplier element 207, many photons are detected, whereas fewer photons are detected in the second angle range α in which the shading portions 120a are close to the light-receiving surface of the photomultiplier element 207. In the first angle range β, within an angle range γ, the number of photons is decreased. Hereinafter, the measurement of photons in the first angle range β may be referred to as a photon count, whereas the measurement of photons in the second angle range α may also be referred to as a dark count.

As shown in FIG. 11B, while the sample analysis substrate 100 has a constant rotational angular velocity irrespective of the rotation angle, the clock counts are also constant. However, as shown in FIG. 11B, during one complete turn of the sample analysis substrate 100, the clock count decreases at every predetermined angle. For example, in the clock count distribution shown in FIG. 11B, the counting time decreases for a total of six times. This means that, while the sample analysis substrate 100 makes one complete turn, the rotation becomes faster in six points to result in larger angular velocities.

From FIG. 11B, it can be seen that the clock count decreases in the angle range γ, thus resulting in a shorter counting time for the number of photons. This indicates that, in the photon count distribution shown in FIG. 11A, the decreased photon count in the angle range γ is not because of a lowered luminescence intensity, but because of a shorter time of measurement.

By correcting the photon count distribution across rotation angles by using the clock count distribution, the control circuit 205 calculates a corrected photon count distribution signal. Specifically, measurement values of photon counts and measurement values of clock counts for the phase ranges θ0 to θk as stored in the memory are read out, and subjected to computation. This computation may be performed after the luminescence measurements, or consecutively performed during the luminescence measurements, for example. Given a photon count distribution value Cr for the phase ranges θ0 to θk ($0 \leq r < k$), and a clock count distribution value $T_r$, as indicated by Expression (2) below, a corrected photon count value $CC_r$ is obtained by dividing $C_r$ with $T_r$. This computation is performed across the phase ranges 0 to k, whereby a correct photon count distribution signal is obtained. For example, if k is from 0 to 191, a photon count distribution signal which is corrected with a resolving power of 1.875° is obtained. From the corrected photon count distribution signal thus obtained, the control circuit 205 may extract e.g. measurement values of photons in the first angle range β, and determine a sum or an average of measurement values, thereby calculating a measurement value C' of luminescence occurring from the sample.

$$CC_r = \frac{C_r}{T_r} \quad (2)$$

Figure 12:
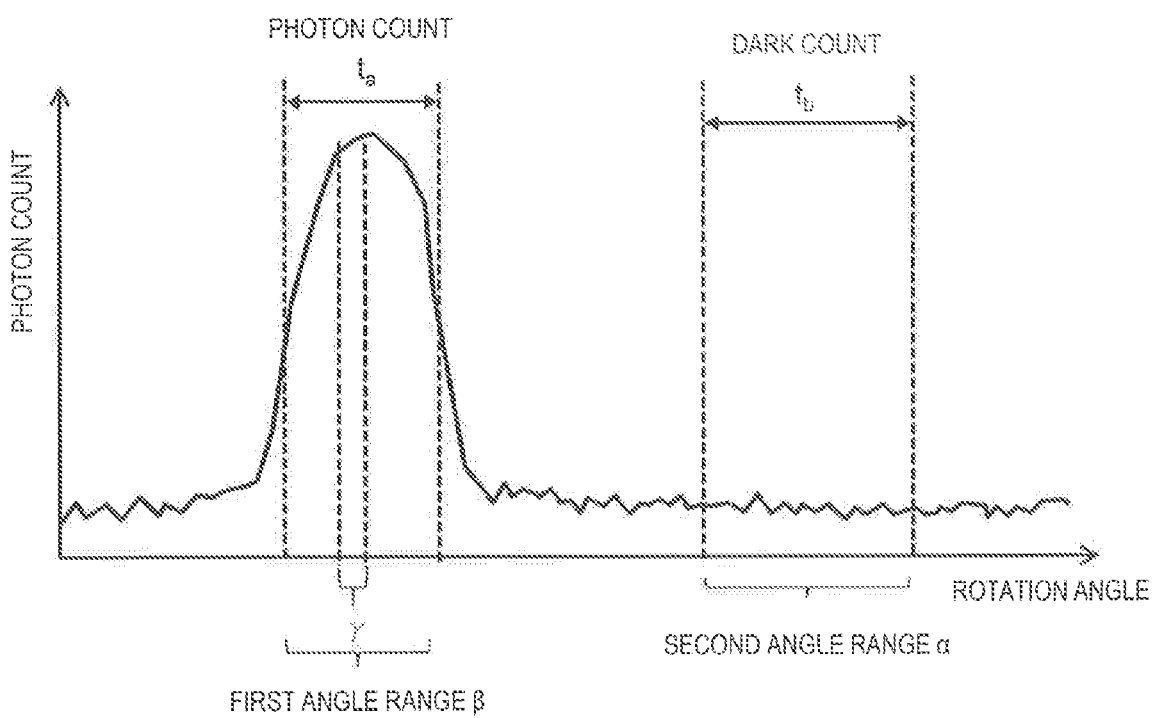
FIG. 12 is a diagram showing an exemplary corrected photon count distribution across rotation angles in the range from 0° to 359°.

FIG. 12 shows a corrected photon count distribution across rotation angles in the phase ranges θ0 to θk (0° to 359°. As shown in FIG. 12, the decrease in the number of photons in the angle range γ has been corrected for. Therefore, by performing such computations, it is possible to reduce measurement errors as to the number of photons due to fluctuations in the angular velocity depending on the rotation angle of the sample analysis substrate, thus enabling more accurate measurement of luminescence intensity of the sample.

The control circuit 205 may use the corrected photon count distribution signal which has thus been obtained to further remove influences of noises in the photomultiplier element 207, in calculating a measurement value of the luminescence of the sample. As shown in FIG. 12, in the corrected photon count distribution signal, ideally, no photons are to be detected in the second angle range α where the shading portions 120a are close to the light-receiving surface of the photomultiplier element 207. However, in actual measurements, counts that are ascribable to noises in the photomultiplier element 207 may be observed, and stray light resulting from the measurement room not being a perfect darkroom may be detected by the photomultiplier element 207. The counts due to such noises may vary depending on the ambient temperature during the measurement. Therefore, as has been described in the first embodiment, in the corrected photon count distribution, the control circuit 205 may correct the number of photons as obtained while detecting the measurement chamber 103 by using the number of photons as obtained while detecting the shading portions 120a. Specifically, from the first angle range β and the second angle range α, at least one first measurement value and at least one second measurement value may be respectively determined, and the at least one first measurement value may be corrected with the at least one second measurement value. The correct can be performed by using Expression (1), as has been described with respect to the first embodiment.

(Operation of Sample Analysis System)

The sample analysis system 500 according to the present embodiment can also operate in similar manners to the first embodiment.

First, as shown in FIG. 6 and in a similar manner to the first embodiment, steps S1 and S2 are performed to introduce a sample onto the sample analysis substrate, and step S3 is performed to transfer the sample to the measurement chamber. Next, measurements of the number of photons associated with luminescence are taken.

[Step S4]

The shutter 202 is opened, and the sample analysis substrate 100 is rotated. The shutter 202 may be opened only after the rotating sample analysis substrate 100 has attained constant rotation.

[Step S5]

By using the photodetector 209, luminescence occurring from the label substance 307 of the labeled antibody 308 bound to the composite 310, being contained in magnetic particles 311, is detected. Specifically, the photomultiplier element 207 of the photodetector 209 generates a pulse signal in accordance with photons from luminescence; and, by using a rotation angle signal which is output from the rotation angle detection circuit 204, the photon counter 208 counts the number of photons and the number of pulses in the reference clock signal for each of phase ranges θ0 to θk. The control circuit 205 consecutively receives the respective numbers of photons for the phase ranges θ0 to θk and measurement values of the number of pulses in the reference clock signal, and stores them to memory.

[Step S6]

After detecting luminescence for a certain period of time, the shutter 202 is closed, and detection is ended.

(4) A Process of Correcting Measurement Values

[Step S7]

From the memory, the control circuit 205 reads out photon count distribution values and clock count distribution values for the phase ranges θ0 to θk, that is, across rotation angles, and as described above, a photon count distribution signal across rotation angles that has been corrected so that the counting time for the number of photons per unit rotation angle of the sample analysis substrate is equal.

Thereafter, measurement values of photons in the first angle range β are extracted, and a sum or an average of measurement values is determined, whereby a measurement value C' of luminescence occurring from the sample is calculated. Furthermore, a measurement value C may be determined in accordance with Expression (2).

(5) A Process of Displaying Measurement Value

[Step S8]

On the display device 210, the measurement value C'(C) and/or index values concerning the amount, concentration, etc., of antigen as determined by using the measurement value C'(C) is displayed.

(Effects)

With the sample analysis device, sample analysis system, and method of measuring luminescence according to the present embodiment, a reference clock signal, a rotation angle signal, and a photon pulse signal are used to calculate a photon count distribution signal across rotation angles that has been corrected so that the counting time for the number of photons per unit rotation angle is equal. As a result, even when the rotational angular velocity of the sample analysis substrate changes during one complete turn, influences of the changing angular velocity can be suppressed so as to enable accurate measurement of subtle luminescence intensities of the sample. Moreover, by correcting a measurement value from luminescence of the sample with a shaded measurement value, it is possible to suppress influences of fluctuations in the measurement value due to temperature changes in the photomultiplier element and/or any stray light or the like which is not luminescence of the sample during measurement, thus enabling highly accurate measurement.

(Variants)

In the above embodiment, the control circuits 205 counts the photon pulse signal and the reference clock signal on the basis of a rotation angle signal, and calculates a photon count distribution and a clock count distribution across rotation angles. Alternatively, the photon counter 208 may count the photon pulse signal and the rotation angle signal on the basis of a reference clock signal, and calculate a photon count distribution and a rotation angle distribution on the time axis. Also in this case, the control circuit 205 may correct the photon count distribution with the rotation angle distribution, and calculate a corrected photon count distribution signal.

Although the above embodiment illustrates that the sample analysis system employs a method of analysis utilizing magnetic particles, luminescence of the sample or a label substance that has bound to the sample may be detected without even using magnetic particles and without performing B/F separation. In this case, the sample analysis substrate 100 may not have a magnet.

A sample analysis device, a sample analysis system, and a method of measuring luminescence of a sample as disclosed in the present application are applicable to the analysis of a specific component in an analyte utilizing any of various reactions.

This application is based on Japanese Patent Applications No. 2017-061567 filed on Mar. 24, 2018 and No. 2017-061568 filed on Mar. 24, 2018, the entire contents of which are hereby incorporated by reference.

While the present subject matter has been described with respect to preferred embodiments thereof, it will be apparent to those skilled in the art that the disclosed subject matter may be modified in numerous ways and may assume many embodiments other than those specifically described above. Accordingly, it is intended by the appended claims to cover all modifications of the present subject matter that fall within the true spirit and scope of the present subject matter.

What is claimed is:

1. A sample analysis system comprising:
   a sample analysis substrate including a reaction chamber, a measurement chamber, a channel coupling the reaction chamber with the measurement chamber, and a shading portion, the measurement chamber having a window; and
   a sample analysis device which rotates the sample analysis substrate to transfer a sample introduced into the reaction chamber to the measurement chamber via the channel to cause the sample to undergo luminescence in the measurement chamber and which measures the luminescence, wherein
   the sample analysis device comprises:
      a motor to rotate the sample analysis substrate with the sample introduced thereon around a rotation axis of the sample analysis substrate;
      a drive circuit to drive the motor;
      a photodetector to measure a number of photons associated with the luminescence from the sample being transmitted through the window of the measurement chamber, the photodetector having a light-receiving surface; and
      a control circuit configured to calculate a measurement value of the luminescence of the sample, wherein
   the control circuit is configured to actuate the drive motor to rotate the sample analysis substrate so as to position the measurement chamber over the light-receiving surface of the photodetector and to position the shading portion over the light-receiving surface of the photodetector;
   the photodetector outputs at least one first measurement value and at least one second measurement value while the sample analysis substrate rotates, the at least one first measurement value being obtained when the measurement chamber passes over the light-receiving surface of the photodetector, and the at least one second measurement value being obtained when the shading portion passes over the light-receiving surface of the photodetector; and
   the control circuit calculates the measurement value of the luminescence of the sample by correcting the at least one first measurement value with the at least one second measurement value.

2. The sample analysis system of claim 1, wherein the sample analysis device further comprises a rotation angle detection circuit to detect a rotation angle of the sample analysis substrate and generate a rotation angle signal, wherein,
   the photodetector outputs a plurality of measurement values obtained through one 360 degree turn of the sample analysis substrate; and
   the control circuit compares each of the plurality of measurement values against a first threshold and against a second threshold, and determines any one of the plurality of measurement values that is equal to or greater than the first threshold to be the at least one first measurement value and any one of the plurality of measurement values that is equal to or less than the second threshold to be the at least one second measurement value.

3. The sample analysis system of claim 1, wherein the sample analysis device further comprising a rotation angle detection circuit to detect a rotation angle of the sample analysis substrate and generate a rotation angle signal, wherein,
   the photodetector outputs a plurality of measurement values obtained while the sample analysis substrate makes one 360 degree turn; and
   the at least one first measurement value corresponds to the luminescence measured by the photodetector when the rotation angle is in a first angle range, and the at least one second measurement value corresponds to the luminescence measured by the photodetector when the rotation angle is in a second angle range.

4. The sample analysis system of claim 3, wherein the second angle range is greater than the first angle range.

5. The sample analysis system of claim 3, wherein the control circuit compares against a third threshold a measurement value which is measured by the photodetector when the rotation angle is not in the first angle range, and generates a signal indicating a measurement error when the measurement value is equal to or greater than the third threshold.

6. The sample analysis system of claim 1, wherein the sample analysis device further comprises a rotation angle detection circuit to detect a rotation angle of the sample analysis substrate and generate a rotation angle signal, wherein,
   the sample analysis substrate includes another measurement chamber in which another sample to undergo luminescence is retained;
   the photodetector further outputs at least one third measurement value while the sample analysis substrate makes one 360 degree turn; and
   the control circuit calculates a measurement value of the luminescence of the other sample by correcting the at least one third measurement value with the at least one second measurement value.

7. The sample analysis system of claim 1, wherein the photodetector includes: a photomultiplier element to receive a photon or photons and generate a pulse signal or pulse signals in accordance with the number of photons; and a photon counter to count the pulse signal.

8. The sample analysis system of claim 1, wherein the sample analysis device further comprises:
- a rotation angle detection circuit to detect a rotation angle of the sample analysis substrate and generate a rotation angle signal; and
- a reference clock generation circuit to generate a reference clock signal, wherein,
- the photodetector includes a photomultiplier element to generate a photon pulse signal in accordance with the number of photons; and
- the control circuit is configured to calculate a photon count distribution signal across rotation angles that has been corrected so that an equal counting time exists for the number of photons per unit rotation angle, the control circuit correcting the photon count distribution signal based on the rotation angle, the reference clock signal and the photon pulse signal.

9. The sample analysis system of claim 8, wherein, the control circuit:
- counts the photon pulse signal on the basis of the rotation angle signal and calculates a photon count distribution across rotation angles,
- counts the reference clock signal on the basis of the rotation angle signal and calculates a clock count distribution across rotation angles, and
- corrects the photon count distribution with the clock count distribution to calculate the corrected photon count distribution signal.

10. The sample analysis system of claim 8, wherein, the control circuit:
- counts the photon pulse signal on the basis of the reference clock signal and calculates a photon count distribution on the time axis,
- counts the rotation angle signal on the basis of the reference clock signal and calculates a rotation angle distribution on the time axis, and
- corrects the photon count distribution with the rotation angle distribution to calculate the corrected photon count distribution signal.

11. The sample analysis system of claim 8, wherein, the control circuit calculates a measurement value of the luminescence of the sample by correcting a first measurement value which exists in the corrected photon count distribution signal when the rotation angle is in a first angle range with a second measurement value which exists in the corrected photon count distribution signal when the rotation angle is in a second angle range.

* * * * *